US012630497B2

(12) United States Patent
Lee et al.

(10) Patent No.: US 12,630,497 B2
(45) Date of Patent: May 19, 2026

(54) COMPOUND HAVING MALATE DEHYDROGENASE INHIBITORY ACTIVITY AND PHARMACEUTICAL COMPOSITION FOR PREVENTING OR TREATING CANCER COMPRISING SAME AS ACTIVE INGREDIENT

(71) Applicants: DONGGUK UNIVERSITY INDUSTRY-ACADEMIC COOPERATION FOUNDATION, Seoul (KR); KOREA RESEARCH INSTITUTE OF BIOSCIENCE AND BIOTECHNOLOGY, Daejeon (KR)

(72) Inventors: Kyeong Lee, Gyeonggi-do (KR); Mi Sun Won, Daejeon (KR); Hyun Seung Ban, Daejeon (KR); Minkyoung Kim, Gyeonggi-do (KR); Bo Kyung Kim, Daejeon (KR)

(73) Assignees: DONGGUK UNIVERSITY INDUSTRY-ACADEMIC COOPERATION FOUNDATION, Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 16/491,237

(22) PCT Filed: Mar. 9, 2018

(86) PCT No.: PCT/KR2018/002861

§ 371 (c)(1),
(2) Date: Sep. 5, 2019

(87) PCT Pub. No.: WO2018/164549

PCT Pub. Date: Sep. 13, 2018

(65) Prior Publication Data

US 2020/0031764 A1 Jan. 30, 2020

(30) Foreign Application Priority Data

Mar. 9, 2017 (KR) ........................ 10-2017-0029916
Mar. 8, 2018 (KR) ........................ 10-2018-0027397

(51) Int. Cl.

| | |
|---|---|
| ***C07C 235/38*** | (2006.01) |
| ***A61P 35/00*** | (2006.01) |
| ***C07D 213/72*** | (2006.01) |
| ***C07D 241/04*** | (2006.01) |
| ***C07D 249/18*** | (2006.01) |

(52) U.S. Cl.
CPC ............ *C07C 235/38* (2013.01); *A61P 35/00* (2018.01); *C07D 213/72* (2013.01); *C07D 241/04* (2013.01); *C07D 249/18* (2013.01)

(58) Field of Classification Search
CPC ..... C07C 235/38; A61P 35/00; C07D 235/38; C07D 249/18; C07D 241/04; C07D 213/72
See application file for complete search history.

(56) References Cited

U.S. PATENT DOCUMENTS 8,394,799 B2 * 3/2013 Lee ....................... C07C 237/42 514/237.8

FOREIGN PATENT DOCUMENTS

| | | |
|---|---|---|
| KR | 20130033989 A | 4/2013 |
| KR | 20140140904 A | 12/2014 |
| KR | 20150088205 A | 7/2015 |

OTHER PUBLICATIONS

Cancer and Metastasis Reviews (1998), 17(1), 91-106.*
Science (1999), vol. 286, 531-537.*
Naik et al., Journal of Medicinal Chemistry, 2012, 55, p. 10564-10571.*
Registry No. 876533-59-4, File REGISTRY on STN, Mar. 13, 2006.*
Registry No. 640242-40-6, File REGISTRY on CAPLUS, entered STN: Jan. 22, 2004.*
Registry No. 900735-73-1, File REGISTRY on STN, entered STN Aug. 11, 2006.*
Kyeong Lee, et al., "Identification of Malate Dehydrogenase 2 as a Target Protein of the HIF-1 Inhibitor LW6 using Chemical Probes", Angewandte Chemie International ed., 2013, vol. 52, e. 10286-10289.
Boovanahalli, S. K., et al., "Synthesis of (aryloxyacetylamino)-isonicotinic/ nicotinic acid analogues as potent hypoxia-inducible factor (HIF)-1a Inhibitors", Bioorganic & Medicinal Chemistry Letters, 2007, vol. 17, e. 6305-6310.
Naik, R, et al., "Methyl 3-(3-(4-(2,4,4-Trimethylpentan-2-yl)phenoxy)- 1-9,11 propanamido)benzoate as a Novel and Dual Malate Dehydrogenase (MDH) 1/2 Inhibitor Targeting Cancer Metabolism", Journal of Medicinal Chemistry, 2017, vol. 60, e. 8631-8646.

* cited by examiner

*Primary Examiner* — Rebecca L Anderson
(74) *Attorney, Agent, or Firm* — Revolution IP, PLLC

(57) ABSTRACT

The present invention relates to a compound exhibiting inhibitory activity of at least one of malate dehydrogenases I (MDH1) and malate dehydrogenases 2 (MDH2), and a pharmaceutical composition for preventing or treating cancer comprising the same as an active ingredient. The inventors of the present invention have experimentally confirmed that the compound exhibiting the MDH1 and/or MDH2 inhibitory activity has an inhibitory effect on mitochondrial respiration in cancer cells, an excellent inhibitory effect on cancer cell growth, etc. Thus, the compound of the present invention is expected to be effectively used as a pharmaceutical composition for treating cancer.

4 Claims, 9 Drawing Sheets

1, 2, 3-1 - 3-34, 4, 5, 6-1 - 6-9, 7, 8, 9-1 - 9-9

COMPOUND HAVING MALATE DEHYDROGENASE INHIBITORY ACTIVITY AND PHARMACEUTICAL COMPOSITION FOR PREVENTING OR TREATING CANCER COMPRISING SAME AS ACTIVE INGREDIENT

CROSS-REFERENCE TO RELATED APPLICATIONS

This application is the U.S. national phase application filed under 35 U.S.C. § 371 claiming benefit to International Patent Application No. PCT/KR2018/002861, filed on Mar. 9, 2018, which claims priority to Korean provisional application no. 10-2017-0029916, filed Mar. 9, 2017 and Korean provisional application no. 10-2018-0027397, filed Mar. 8, 2018, the disclosures of which are incorporated herein by reference in their entirety.

TECHNICAL FIELD

The present invention relates to a novel compound exhibiting inhibitory activity of malate dehydrogenase 1 (MDH1) or malate dehydrogenase 2 (MDH2) and a pharmaceutical composition for preventing or treating cancer including the same as an active ingredient.

This application claims priority to and the benefits of Korean Patent Application No. 10-2017-0029916, filed on Mar. 9, 2017, and Korean Patent Application No. 10-2018-0027397, filed on Mar. 8, 2018, the disclosures of which are incorporated herein by reference in their entireties.

BACKGROUND ART

Compared to normal cells, cancer cells show various changes in metabolism, such as aerobic glycolysis, an increase in fatty acid synthesis, rapid glutamine metabolism, etc. Particularly, the activation of glycolysis causes changes in ATP synthesis, biomaterial biosynthesis and oxidation-reduction regulation. The malate-aspartate shuttle is a mechanism playing an important role in delivering NADH in the cytoplasm, which is generated in glycolysis, to mitochondria. The malate-aspartate shuttle includes MDHs present in the cytoplasm and mitochondria and glutamate oxaloacetate transaminases (GOTs). Aminooxyacetic acid (AOA), which is an inhibitor of the malate-aspartate shuttle prevents glucose from becoming a product of the tricarboxylic acid cycle (TCA), thereby inhibiting the proliferation of breast cancer cells. In addition, it has been reported that, in pancreatic cancer, the acetylation of mitochondrial GOT2 present in mitochondria promotes NADH transfer through malate-aspartate, and is involved in ATP synthesis required for the proliferation of cancer cells.

Meanwhile, MDH1 and MDH2 isoenzymes generated by different MDH genes are present in the cytoplasm and the mitochondrial matrix. MDH1 and MDH2 serve to reversibly convert malate and oxaloacetate (OAA) using the NAD/NADH cofactor system. MDH1 located in the cytoplasm serves to reduce oxalate to malate, resulting in oxidization of NADH to $NAD^+$. In the malate-aspartate shuttle, malate is transferred into the mitochondria, reoxidized to oxalate by mitochondrial MDH2, thereby generating NADH. The generated NADH generates ATP through the electron transport system. In addition to this, TCA cycle-associated MDH2 is involved in ATP synthesis through respiration.

Recently, cancer relevance of MDH1 and MDH2 has been reported, and the fact that MDH1 is needed to maintain the redox state in cells by glutamine metabolism reprogramming in glutamine-dependent pancreatic ductal adenocarcinoma (PDAC) cells has been reported. As a result of MDH1 knockdown, it was observed that PDAC cells died and the proliferation of Erb-B2 receptor tyrosine kinase 2 (ERBB2)-positive BT474 breast cancer cells is inhibited by inhibiting fatty acid synthesis. In addition, it has been reported that prostate cancer cells highly expressing MDH2 exhibit anti-cancer resistance, and relapse-free survival is short, and through the knockdown of MDH2 in a prostate cancer cell line, metabolic inefficiency in the cancer cell line was induced, thus confirming cell proliferation and increased sensitivity to docetaxel. At present, while there are various attempts to treat cancer (Korean Unexamined Patent Application No. 10-2010-0126924), these attempts have a side effect such as resistance, and while a study on cancer relevance of MDH1 and MDH2 has been reported, there is no attempt to develop MDH1 and MDH2 inhibitors as anticancer agents.

Therefore, to solve the conventional problems, while continuing to develop more effective cancer therapeutic substances, the inventors expected that it is possible to develop a MDH1/2 dual inhibitor which simultaneously inhibits MDH1 and MDH2 activities due to the very similar structures of substrate binding sites and activation sites of MDH1 and MDH2, and thus prepared a compound for simultaneously inhibiting MDH1 and MDH2 activities, resulting in firstly inventing a cancer therapeutic agent including the compound. Therefore, the present invention was completed.

DISCLOSURE

Technical Problem

To solve the above-described problem, the inventors verified the cancer preventive or therapeutic effect of the compound that inhibits MDH1 and/or MDH2 activity, and based on this, the present invention was completed.

Therefore, the present invention is directed to providing a compound exhibiting MDH1 and/or MDH2 inhibitory activity, an isomer thereof or a pharmaceutically acceptable salt thereof.

The present invention is also directed to providing a pharmaceutical composition for preventing or treating cancer, which includes a compound exhibiting MDH1 and/or MDH2 inhibitory activity, an isomer thereof or a pharmaceutically acceptable salt thereof as an active ingredient.

However, technical problems to be solved in the present invention are not limited to the above-described problems, and other problems which are not described herein will be fully understood by those of ordinary skill in the art from the following descriptions.

To attain the objects of the present invention, the present invention provides a compound represented by Formula 1 below, an isomer thereof or a pharmaceutically acceptable salt thereof.

[Formula 1]

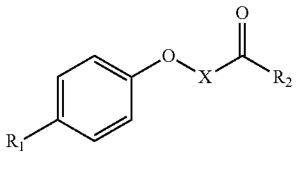

Here, in Formula 1,

X is a methylene group, an ethane group, an ethylene group, an n-propylene group or an isopropylene group;

$R_1$ is a nitro group, a trifluoromethyl group, $C_1$-$C_{20}$ alkyl or $C_1$-$C_{20}$ cycloalkyl; and $R_2$ is

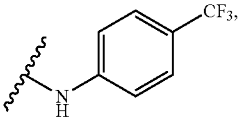

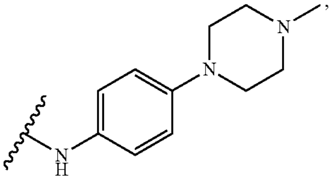

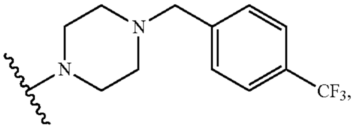

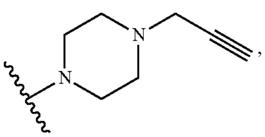,
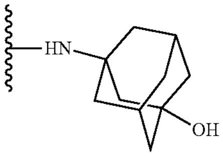,

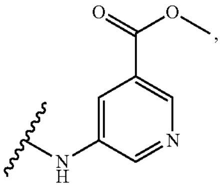,
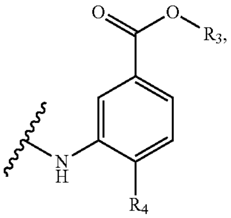

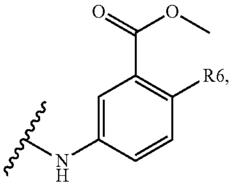
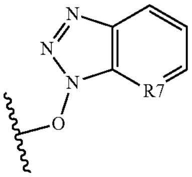
or

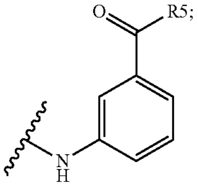

when $R_2$ is

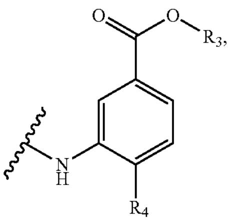

$R_3$ is methyl or 2-propynyl; and $R_4$ is methyl, hydrogen, hydroxyl, methoxy, 2-propynyl,

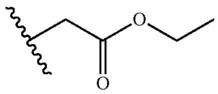,
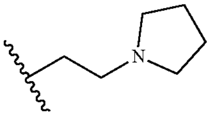,
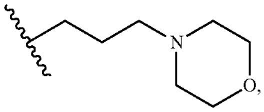
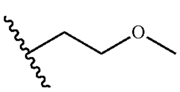,
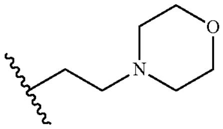, or
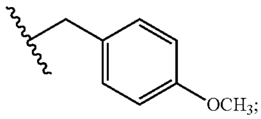

when $R_2$ is

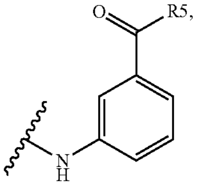

$R_5$ is

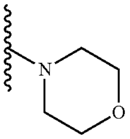,
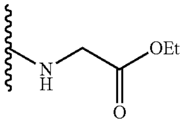
or
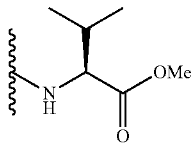, when $R_2$ is

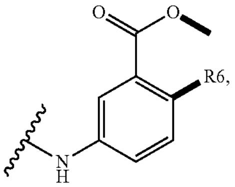

$R_6$ is methyl or hydroxyl; and when $R_2$ is,

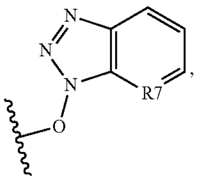

$R_7$ may be C or N.

In one exemplary embodiment of the present invention, $R_1$ may be substituted with adamantyl, tert-butyl, pentyl, cyclopentyl, cyclohexyl, or 2,4,4-trimethylpentane-2-yl.

In addition, in an exemplary embodiment of the present invention, $R_1$ is adamantyl;

X is a methylene group, an ethane group, an ethylene group, a n-propylene group or an isopropylene group; and $R_2$ is

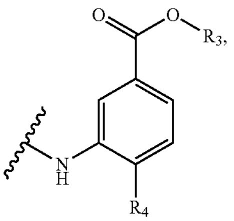

$R_4$ is methyl, hydrogen, hydroxyl,

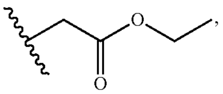

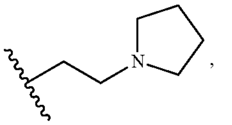

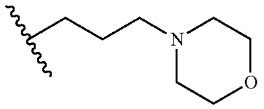

or

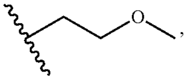

and $R_3$ may be methyl.

In addition, in an exemplary embodiment of the present invention, the compound may be a compound represented by Formula 2 below.

[Formula 2]

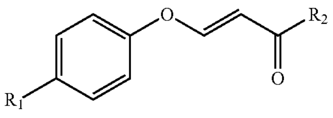

Here, in Formula 2, $R_1$ is adamantyl or tert-butyl; and $R_2$ is

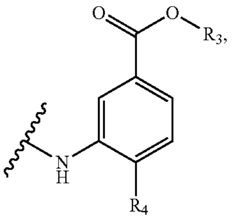

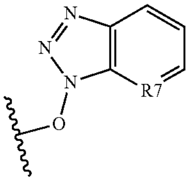

or

-continued

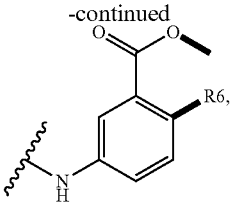

when $R_2$ is

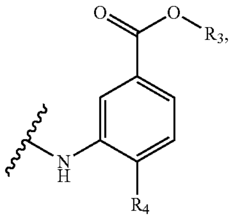

$R_3$ is methyl or 2-propynyl;

$R_4$ is methyl, hydrogen or hydroxyl;

when $R_2$ is

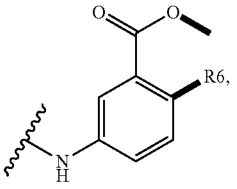

$R_6$ is methyl or hydroxyl; and when $R_2$ is

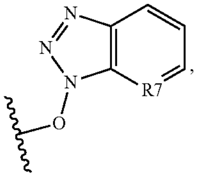

$R_7$ may be C or N.

In addition, in an exemplary embodiment of the present invention, the compound may be a compound represented by Formula 3 below.

[Formula 3]

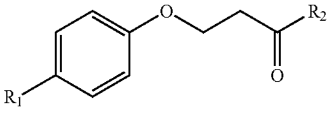

Here, in Formula 3, $R_1$ is a nitro group, a trifluoromethyl group, adamantyl, tert-butyl, pentyl, cyclopentyl, cyclohexyl, or 2,4,4-trimethylpentane-2-yl;

$R_2$ is

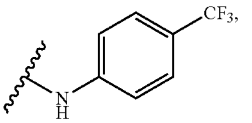

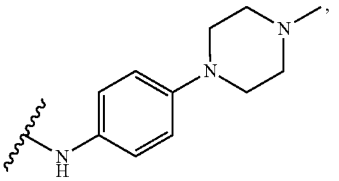

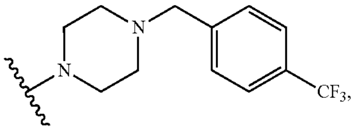

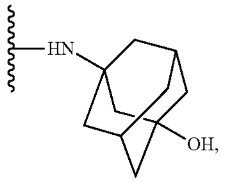

or

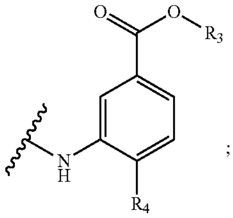

;

when $R_2$ is

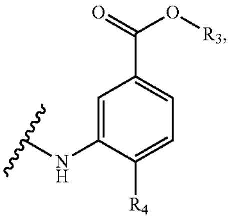

$R_3$ is methyl or 2-propynyl; and $R_4$ may be methyl, hydrogen, hydroxyl, methoxy, 2-propynyl,

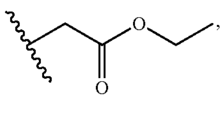

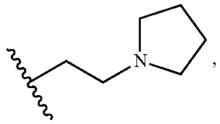

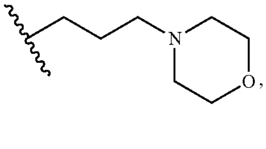

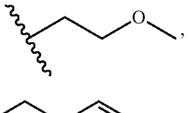

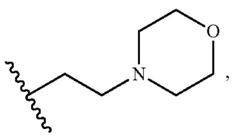

or

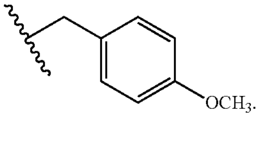

In another exemplary embodiment of the present invention, the compound may be any one or more selected from the group consisting of:

(1) methyl 3-(2-(4-nitrophenoxy)acetamido)benzoate;

(2) methyl 3-(2-(4-(trifluoromethyl)phenoxy)acetamido)benzoate;

(3) methyl 3-(2-(4-tert-butylphenoxy)acetamido)benzoate;

(4) methyl 3-(2-(p-tolyloxy)acetamido)benzoate;

(5) methyl 3-(2-(4-ethylphenoxy)acetamido)benzoate;

(6) methyl 3-(2-(4-propylphenoxy)acetamido)benzoate;

(7) methyl 3-(2-(4-butylphenoxy)acetamido)benzoate;

(8) methyl 3-(2-(4-pentylphenoxy)acetamido)benzoate;

(9) methyl 3-(2-(4-cyclopentylphenoxy)acetamido)benzoate;

(10) methyl 3-(2-(4-cyclohexylphenoxy)acetamido)benzoate;

(11) methyl 3-(2-(4-(2,4,4-trimethylpentan-2-yl)phenoxy)acetamido)benzoate;

(12) methyl 4-hydroxy-3-(2-(4-(2,4,4-trimethylpentan-2-yl)phenoxy)acetamido)benzoate;

(13) N-(4-(trifluoromethyl)phenyl)-2-(4-(2,4,4-trimethylpentan-2-yl)phenoxy)acetamide;

(14) N-(4-(4-methylpiperazin-1-yl)phenyl)-2-(4-(2,4,4-trimethylpentan-2-yl)phenoxy)acetamide;

(15) 1-(4-(4-(trifluoromethyl)benzyl)piperazin-1-yl)-2-(4-(2,4,4-trimethylpentan-2-yl)phenoxy)ethanone;

(16) 1-(4-(prop-2-ynyl)piperazin-1-yl)-2-(4-(2,4,4-trimethylpentan-2-yl)phenoxy)ethanone;

(17) prop-2-ynyl 4-hydroxy-3-(2-(4-(2,4,4-trimethylpentan-2-yl)phenoxy)acetamido)benzoate;

(18) N-(3-hydroxy-adamantan-1-yl)-2-(4-(2,4,4-trimethylpentan-2-yl)phenoxy)acetamide;

(19) methyl 3-(2-(4-adamantan-1-yl-phenoxy)acetamido)benzoate;

(20) methyl 3-(2-(4-adamantan-1-yl-phenoxy)acetamido)-4-hydroxybenzoate;

(21) methyl 3-(2-(4-adamantan-1-yl-phenoxy)acetamido)-4-(2-ethoxy-2-oxoethoxy)benzoate;

(22) methyl 3-(2-(4-adamantan-1-yl-phenoxy)acetamido)-4-(2-(pyrrolidin-1-yl)ethoxy)benzoate;

(23) methyl 3-(2-(4-adamantan-1-yl-phenoxy)acetamido)-4-(3-morpholinopropoxy)benzoate;

(24) methyl 4-methoxy-3-(2-(4-(2,4,4-trimethylpentan-2-yl)phenoxy)acetamido)benzoate;

(25) methyl 4-(2-methoxyethoxy)-3-(2-(4-(2,4,4-trimethylpentan-2-yl)phenoxy)acetamido)benzoate;

(26) methyl 4-(2-morpholinoethoxy)-3-(2-(4-(2,4,4-trimethylpentan-2-yl)phenoxy)acetamido)benzoate;

(27) methyl 4-(prop-2-ynyloxy)-3-(2-(4-(2,4,4-trimethylpentan-2-yl)phenoxy)acetamido)benzoate;

(28) methyl 4-(4-methoxybenzyloxy)-3-(2-(4-(2,4,4-trimethylpentan-2-yl)phenoxy)acetamido)benzoate;

(29) methyl 3-(2-(4-adamantan-1-yl-phenoxy)-2-methylpropanamido)benzoate;

(30) methyl 3-(2-methyl-2-(4-(2,4,4-trimethylpentan-2-yl)phenoxy)propanamido)benzoate;

(31) methyl-4-hydroxy-3-(2-methyl-2-(4-(2,4,4-trimethylpentan-2-yl)phenoxy)propanamido)benzoate;

(32) methyl 3-[4-(4-adamantan-1-yl-phenoxy)butanamido]benzoate;

(33) methyl 3-(4-(4-(2,4,4-trimethylpentan-2-yl)phenoxy)butanamido)benzoate;

(34) methyl 4-hydroxy-3-(4-(4-(2,4,4-trimethylpentan-2-yl)phenoxy)butanamido)benzoate;

(35) (E)-3-[3-(4-adamantan-1-yl-phenoxy)-acryloylamino]-benzoic acid methyl ester;

(36) (E)-3-{3-[4-(2,4,4-trimethylpentan-2-yl)phenoxy] acrylamido}benzoic acid methyl ester;
(37) (E)-methyl 4-methyl-3-(3-(4-(2,4,4-trimethylpentan-2-yl)phenoxy)acrylamido)benzoate;
(38) (E)-methyl 2-methyl-5-(3-(4-(2,4,4-trimethylpentan-2-yl)phenoxy)acrylamido)benzoate;
(39) (E)-methyl 2-hydroxy-5-(3-(4-(2,4,4-trimethylpentan-2-yl)phenoxy)acrylamido)benzoate;
(40) (E)-isopropyl 3-(3-(4-(2,4,4-trimethylpentan-2-yl)phenoxy)acrylamido)benzoate;
(41) ((E)-methyl 2,4-dimethyl-5-(3-(4-(2,4,4-trimethylpentan-2-yl)phenoxy)acrylamido)benzoate;
(42) (E)-3H-[1,2,3]triazolo[4,5-b]pyridin-3-yl 3-(4-(2,4,4-trimethylpentan-2-yl)phenoxy)acrylate;
(43) (E)-1H-benzo[d][1,2,3]triazol-1-yl 3-(4-(2,4,4-trimethylpentan-2-yl)phenoxy)acrylate;
(44) (E)-methyl 4-hydroxy-3-(3-(4-(2,4,4-trimethylpentan-2-yl)phenoxy)acrylamido)benzoate;
(45) methyl 3-(3-(4-(adamantan-1-yl)phenoxy)propanamido)benzoate;
(46) methyl 3-(3-(4-(2,4,4-trimethylpentan-2-yl)phenoxy) propanamido)benzoate;
(47) methyl 4-hydroxy-3-(3-(4-(2,4,4-trimethylpentan-2-yl) phenoxy)propanamido)benzoate;
(48) methyl 4-methyl-3-(3-(4-(2,4,4-trimethylpentan-2-yl) phenoxy)propanamido)benzoate;
(49) methyl 2-methyl-5-(3-(4-(2,4,4-trimethylpentan-2-yl) phenoxy)propanamido)benzoate;
(50) methyl 2-hydroxy-5-(3-(4-(2,4,4-trimethylpentan-2-yl) phenoxy)propanamido)benzoate;
(51) isopropyl 3-(3-(4-(2,4,4-trimethylpentan-2-yl)phenoxy)propanamido)benzoate;
(52) methyl 5-(3-(4-(2,4,4-trimethylpentan-2-yl)phenoxy) propanamido)nicotinate;
(53) N-(3-(morpholine-4-carbonyl)phenyl)-3-(4-(2,4,4-trimethylpentan-2-yl)phenoxy)propanamide;
(54) ethyl 2-(3-(3-(4-(2,4,4-trimethylpentan-2-yl)phenoxy) propanamido)benzamido)acetate; and
(55) (S)-methyl 3-methyl-2-(3-(3-(4-(2,4,4-trimethylpentan-2-yl)phenoxy)propanamido)benzamido)butanoate.

The present invention provides a pharmaceutical composition for preventing or treating cancer, which includes the compound represented by Formula 1, an isomer thereof or a pharmaceutically acceptable salt thereof as an active ingredient.

In an exemplary embodiment of the present invention, the composition may inhibit the activity of MDH1 and/or MDH2.

In an exemplary embodiment of the present invention, the composition may simultaneously inhibit MDH1 and MDH2 activities.

The present invention provides a method for preventing or treating cancer, which includes administering the pharmaceutical composition to an individual.

The present invention provides a use of a composition including the compound, an isomer thereof or a pharmaceutically acceptable salt thereof as an active ingredient for preventing or treating cancer.

Advantageous Effects

The present invention relates to a compound exhibiting MDH1 and/or MDH2 inhibitory activity and a pharmaceutical composition for preventing or treating cancer, which includes the same as an active ingredient. The inventors have experimentally confirmed excellent effects of the compound exhibiting MDH1 and/or MDH2 inhibitory activity on inhibition of mitochondrial respiration in cancer cells and inhibition of cancer cell growth, and thus the compound of the present invention is expected to be effectively used as a pharmaceutical composition for treating cancer.

MODES OF THE INVENTION

Figure 1:
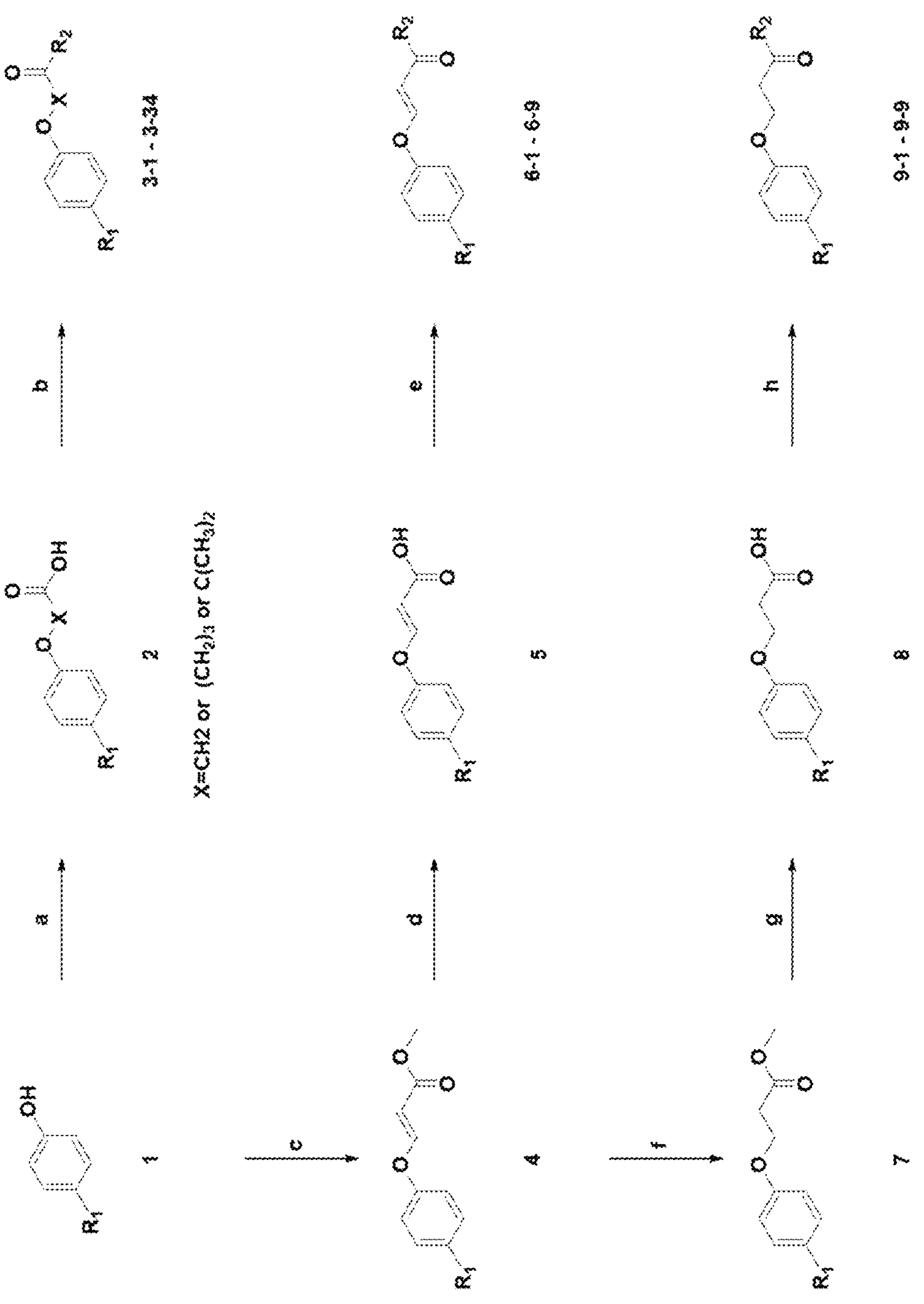
FIG. 1 schematically shows a process of synthesizing 55 types of compounds of the present invention (Compounds 3-1 to 3-34, 6-1 to 6-10 and 9-1 to 9-11).

The inventors specifically confirmed that a compound of the present invention has inhibitory effects on HIF-1α expression and mitochondrial respiration in cancer cells, and an excellent inhibitory effect on cancer cell growth, on the basis of MDH1/2 expression inhibitory activity exhibited when a compound prepared in an exemplary embodiment is treated, and the present invention was completed based on this.

Hereinafter, the present invention will be described in detail.

The present invention provides a compound represented by Formula 1 below, an isomer thereof or a pharmaceutically acceptable salt thereof.

[Formula 1]

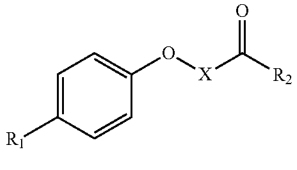

Here, in Formula 1,

X is a methylene group, an ethane group, an ethylene group, an n-propylene group or an isopropylene group;

$R_1$ is a nitro group, a trifluoromethyl group, $C_1$-$C_{20}$ alkyl or $C_1$-$C_{20}$ cycloalkyl; and
$R_2$ may be
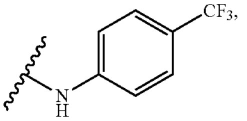
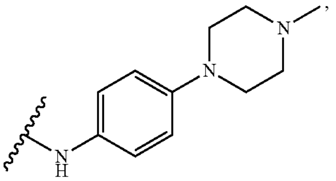
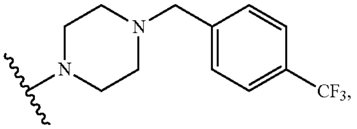
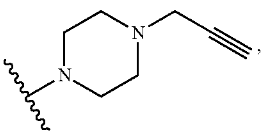
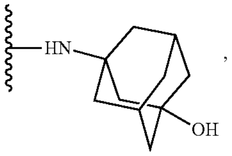
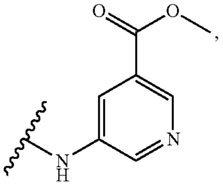
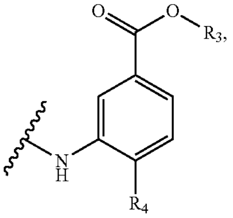
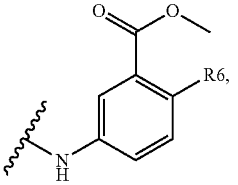
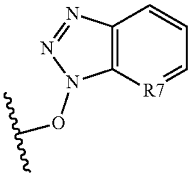
or
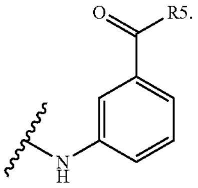
In addition, when $R_2$ is
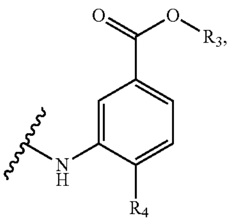
$R_3$ is methyl or 2-propynyl; and
$R_4$ may be methyl, hydrogen, hydroxyl, methoxy, 2-propynyl,
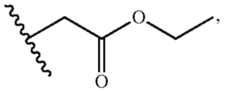
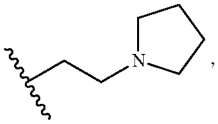
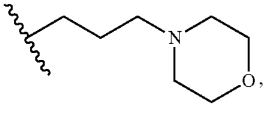
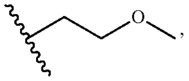
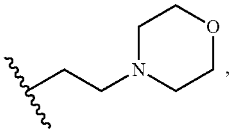
or
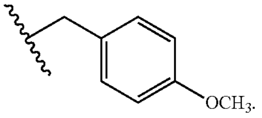
When $R_2$ is
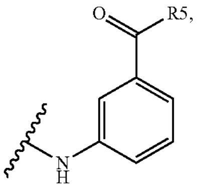
$R_5$ may be
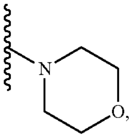
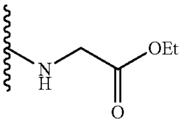
or
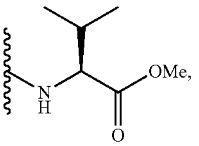
When $R_2$ is
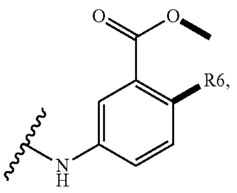
$R_6$ may be methyl or hydroxyl.

When $R_2$ is

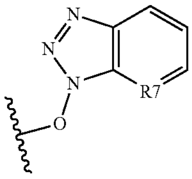, $R_7$ may be C or N.

Preferably, in Formula 1, $R_1$ is adamantyl, tert-butyl, pentyl, cyclopentyl, cyclohexyl, or 2,4,4-trimethylpentane-2-yl.

More preferably, in Formula 1, $R_1$ is adamantyl;

X is a methylene group, an ethane group, an ethylene group, a n-propylene group or an isopropylene group; and $R_2$ is

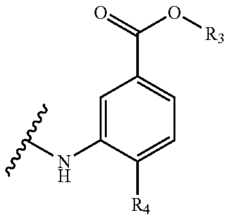,

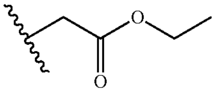,

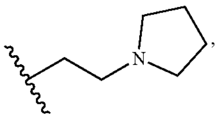, or

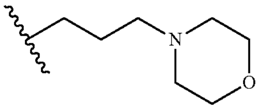, and $R_3$ may be methyl.

More preferably, the compound may be a compound represented by Formula 2 below.

[Formula 2]

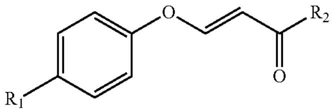

Here, in Formula 2, $R_1$ is adamantyl or tert-butyl; and $R_2$ is

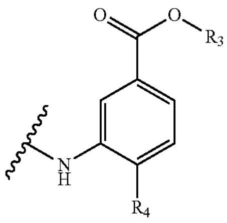

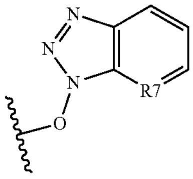

or

-continued

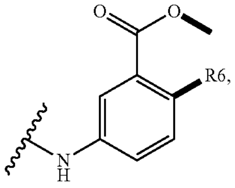

when $R_2$ is

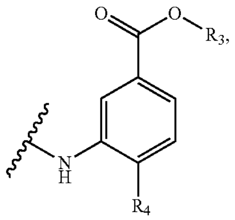

$R_3$ is methyl or 2-propynyl;

$R_4$ is methyl, hydrogen or hydroxyl;

when $R_2$ is

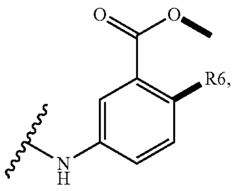

$R_6$ is methyl or hydroxyl; and when $R_2$ is

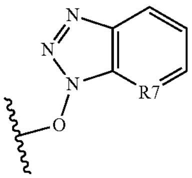, $R_7$ may be C or N.

Preferably, the compound may be compound represented by Formula 3 below.

[Formula 3]

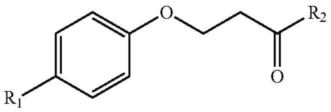

Here, in Formula 3, $R_1$ is a nitro group, a trifluoromethyl group, adamantyl, tert-butyl, pentyl, cyclopentyl, cyclohexyl, or 2,4,4-trimethylpentane-2-yl;

$R_2$ is

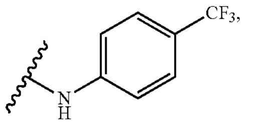

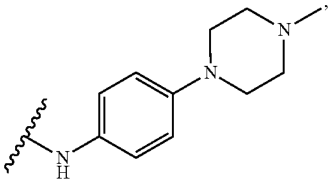

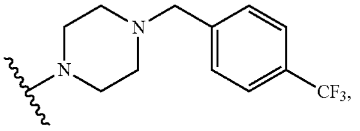

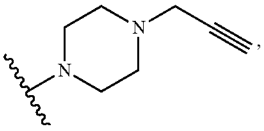

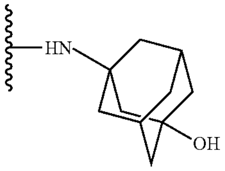

, or

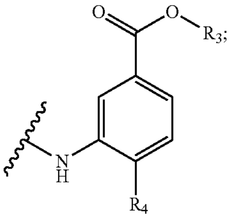

when $R_2$ is

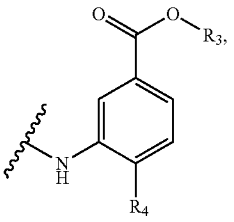

$R_3$ is methyl or 2-propynyl; and $R_4$ may be methyl, hydrogen, hydroxyl, methoxy, 2-propynyl,

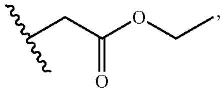

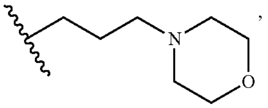

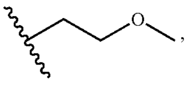

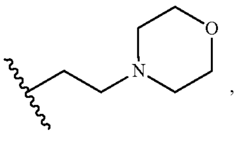

, or

-continued

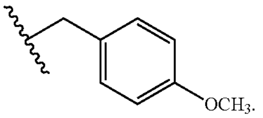

Hereinafter, the definition of various substituents for preparing compounds according to the invention will be provided.

The term "$C_1$-$C_{20}$ alkyl" refers to a monovalent alkyl group having 1 to 20 carbon atoms. This term may be a functional group such as methyl, ethyl, n-propyl, i-propyl, n-butyl, i-butyl, tert-butyl, or n-hexyl.

The term "$C_1$-$C_{20}$ cycloalkyl" used herein refers to a saturated hydrocarbon ring compound having a single ring (e.g., cyclohexyl) or multiple condensed rings (e.g., norbonyl), and includes cyclopentyl, cyclohexyl, norbonyl, and adamantane.

The term "methylene group" used herein means bonding in the form of $-(CH_2)-$, and means a form when one carbon binds to X in Formula 1 of the present invention. n is 1 or 2.

The term "ethane group" used herein mean bonding in the form of $-(C_2H_4)-$, and means the form when two carbons bind to X in Formula 1 of the present invention.

The term "ethylene group" used herein means bonding in the form of $-(C_2H_2)-$, and means the form when two carbons bind to X in Formula 1 of the present invention.

The term "n-propylene group" used herein means bonding in the form of $-(C_3H_6)-$, and means the form when three carbons bind to X in a linear type in Formula 1 of the present invention.

The term "isopropylene group" used herein means bonding in the form of $-(C_3H_6)-$, and means the form when three carbons bind to X in a branched or side chain type in Formula 1 of the present invention.

The term "2-propynyl" used herein means $-CH_2C{\equiv}CH$, and a linear hydrocarbon group having three carbon atoms, which includes an unsaturated carbon binding to the end by a triple bond.

A substituent including the alkyl described in the present invention and an alkyl moiety other than this includes a linear or branched type.

An exemplary embodiment of the compound represented by Formula 1 according to the present invention is as follows:

(1) methyl 3-(2-(4-nitrophenoxy)acetamido)benzoate;
(2) methyl 3-(2-(4-(trifluoromethyl)phenoxy)acetamido)benzoate;
(3) methyl 3-(2-(4-tert-butylphenoxy)acetamido)benzoate;
(4) methyl 3-(2-(p-tolyloxy)acetamido)benzoate;
(5) methyl 3-(2-(4-ethylphenoxy)acetamido)benzoate;
(6) methyl 3-(2-(4-propylphenoxy)acetamido)benzoate;
(7) methyl 3-(2-(4-butylphenoxy)acetamido)benzoate;
(8) methyl 3-(2-(4-pentylphenoxy)acetamido)benzoate;
(9) methyl 3-(2-(4-cyclopentylphenoxy)acetamido)benzoate;
(10) methyl 3-(2-(4-cyclohexylphenoxy)acetamido)benzoate;
(11) methyl 3-(2-(4-(2,4,4-trimethylpentan-2-yl)phenoxy)acetamido)benzoate;
(12) methyl 4-hydroxy-3-(2-(4-(2,4,4-trimethylpentan-2-yl)phenoxy)acetamido)benzoate;
(13) N-(4-(trifluoromethyl)phenyl)-2-(4-(2,4,4-trimethylpentan-2-yl)phenoxy)acetamide;

(14) N-(4-(4-methylpiperazin-1-yl)phenyl)-2-(4-(2,4,4-trimethylpentan-2-yl)phenoxy)acetamide;
(15) 1-(4-(4-(trifluoromethyl)benzyl)piperazin-1-yl)-2-(4-(2,4,4-trimethylpentan-2-yl)phenoxy)ethanone;
(16) 1-(4-(prop-2-ynyl)piperazin-1-yl)-2-(4-(2,4,4-trimethylpentan-2-yl)phenoxy)ethanone;
(17) prop-2-ynyl 4-hydroxy-3-(2-(4-(2,4,4-trimethylpentan-2-yl)phenoxy)acetamido)benzoate;
(18) N-(3-hydroxy-adamantan-1-yl)-2-(4-(2,4,4-trimethylpentan-2-yl)phenoxy)acetamide;
(19) methyl 3-(2-(4-adamantan-1-yl-phenoxy)acetamido)benzoate;
(20) methyl 3-(2-(4-adamantan-1-yl-phenoxy)acetamido)-4-hydroxybenzoate;
(21) methyl 3-(2-(4-adamantan-1-yl-phenoxy)acetamido)-4-(2-ethoxy-2-oxoethoxy)benzoate;
(22) methyl 3-(2-(4-adamantan-1-yl-phenoxy)acetamido)-4-(2-(pyrrolidin-1-yl)ethoxy)benzoate;
(23) methyl 3-(2-(4-adamantan-1-yl-phenoxy)acetamido)-4-(3-morpholinopropoxy)benzoate;
(24) methyl 4-methoxy-3-(2-(4-(2,4,4-trimethylpentan-2-yl)phenoxy)acetamido)benzoate:
(25) methyl 4-(2-methoxyethoxy)-3-(2-(4-(2,4,4-trimethylpentan-2-yl)phenoxy)acetamido)benzoate;
(26) methyl 4-(2-morpholinoethoxy)-3-(2-(4-(2,4,4-trimethylpentan-2-yl)phenoxy)acetamido)benzoate;
(27) methyl 4-(prop-2-ynyloxy)-3-(2-(4-(2,4,4-trimethylpentan-2-yl)phenoxy)acetamido)benzoate;
(28) methyl 4-(4-methoxybenzyloxy)-3-(2-(4-(2,4,4-trimethylpentan-2-yl)phenoxy)acetamido)benzoate;
(29) methyl 3-(2-(4-adamantan-1-yl-phenoxy)-2-methylpropanamido)benzoate;
(30) methyl 3-(2-methyl-2-(4-(2,4,4-trimethylpentan-2-yl)phenoxy)propanamido)benzoate;
(31) methyl-4-hydroxy-3-(2-methyl-2-(4-(2,4,4-trimethylpentan-2-yl)phenoxy)propanamido)benzoate;
(32) methyl 3-[4-(4-adamantan-1-yl-phenoxy)butanamido]benzoate;
(33) methyl 3-(4-(4-(2,4,4-trimethylpentan-2-yl)phenoxy)butanamido)benzoate;
(34) methyl 4-hydroxy-3-(4-(4-(2,4,4-trimethylpentan-2-yl)phenoxy)butanamido)benzoate;
(35) (E)-3-[3-(4-adamantan-1-yl-phenoxy)-acryloylamino]-benzoic acid
methyl ester;
(36) (E)-3-{3-[4-(2,4,4-trimethylpentan-2-yl)phenoxy]acrylamido}benzoic acid methyl ester;
(37) (E)-methyl 4-methyl-3-(3-(4-(2,4,4-trimethylpentan-2-yl)phenoxy)acrylamido)benzoate;
(38) (E)-methyl 2-methyl-5-(3-(4-(2,4,4-trimethylpentan-2-yl)phenoxy)acrylamido)benzoate;
(39) (E)-methyl 2-hydroxy-5-(3-(4-(2,4,4-trimethylpentan-2-yl)phenoxy)acrylamido)benzoate;
(40) (E)-isopropyl 3-(3-(4-(2,4,4-trimethylpentan-2-yl)phenoxy)acrylamido)benzoate;
(41) ((E)-methyl 2,4-dimethyl-5-(3-(4-(2,4,4-trimethylpentan-2-yl)phenoxy)acrylamido)benzoate;
(42) (E)-3H-[1,2,3]triazolo[4,5-b]pyridin-3-yl 3-(4-(2,4,4-trimethylpentan-2-yl)phenoxy)acrylate;
(43) (E)-1H-benzo[d][1,2,3]triazol-1-yl 3-(4-(2,4,4-trimethylpentan-2-yl)phenoxy)acrylate;
(44) (E)-methyl 4-hydroxy-3-(3-(4-(2,4,4-trimethylpentan-2-yl)phenoxy)acrylamido)benzoate;
(45) methyl 3-(3-(4-(adamantan-1-yl)phenoxy)propanamido)benzoate;
(46) methyl 3-(3-(4-(2,4,4-trimethylpentan-2-yl)phenoxy)propanamido)benzoate;
(47) methyl 4-hydroxy-3-(3-(4-(2,4,4-trimethylpentan-2-yl)phenoxy)propanamido)benzoate;
(48)methyl 4-methyl-3-(3-(4-(2,4,4-trimethylpentan-2-yl)phenoxy)propanamido)benzoate;
(49) methyl 2-methyl-5-(3-(4-(2,4,4-trimethylpentan-2-yl)phenoxy)propanamido)benzoate;
(50) methyl 2-hydroxy-5-(3-(4-(2,4,4-trimethylpentan-2-yl)phenoxy)propanamido)benzoate;
(51) isopropyl 3-(3-(4-(2,4,4-trimethylpentan-2-yl)phenoxy)propanamido)benzoate);
(52) methyl 5-(3-(4-(2,4,4-trimethylpentan-2-yl)phenoxy)propanamido)nicotinate;
(53) N-(3-(morpholine-4-carbonyl)phenyl)-3-(4-(2,4,4-trimethylpentan-2-yl)phenoxy)propanamide;
(54) ethyl 2-(3-(3-(4-(2,4,4-trimethylpentan-2-yl)phenoxy)propanamido)benzamido)acetate; or
(55) (S)-methyl 3-methyl-2-(3-(3-(4-(2,4,4-trimethylpentan-2-yl)phenoxy)propanamido)benzamido)butanoate.

The "pharmaceutically acceptable" used herein means a compound or composition which is suitable for use in contact with the tissue of a subject (e.g., a human) because the benefit/risk ratio is reasonable without excessive toxicity, irritation, allergic reactions or other problems or complications, and in the category of sound medical judgment.

The term "salt" used herein is an acid addition salt formed by a pharmaceutically acceptable free acid. The acid addition salt is obtained from inorganic acids such as hydrochloric acid, nitric acid, phosphoric acid, sulfuric acid, hydrobromic acid, hydroiodic acid, nitrous acid or phosphorous acid, aliphatic mono- and di-carboxylates, phenyl-substituted alkanoates, hydroxy alkanoates and alkane dioates, and non-toxic organic acids such as aromatic acids, aliphatic and aromatic sulfonic acids. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxylbenzoates, methoxybenzoates, phthalates, terephthalates, benzenesulfonates, toluenesulfonates, chlorobenzenesulfonates, xylenesulfonates, chlorobenzenesulfonates, xylenesulfonates, phenylacetates, phenylpropionates, phenylbutyrates, citrates, lactates, β-hydroxylbutyrates, glycolates, malates, tartrates, methanesulfonates, propanesulfonates, naphthalene-1-sulfonates, naphthalene-2-sulfonates or mandelates.

The acid addition salt according to the present invention may be prepared by a conventional method, for example, by dissolving the compound represented by Formula 1 of the present invention in an excessive amount of acid aqueous solution, and precipitating the salt using a water-miscible organic solvent, for example, methanol, ethanol, acetone or acetonitrile. In addition, the acid addition salt may be prepared by evaporating a solvent or an excessive acid amount from the mixture, and then suction-filtering a dried or precipitated salt.

In addition, a pharmaceutically acceptable metal salt may be prepared using a base. An alkali metal or alkali earth metal salt may be obtained by, for example, dissolving a compound in an excessive amount of an alkali metal hydroxide or alkali earth metal hydroxide solution, filtering an insoluble compound salt, and evaporating and drying the filtrate. Here, as a metal salt, a sodium, potassium or calcium salt is suitable for pharmaceuticals. The corresponding silver salt is obtained by reacting an alkali metal or alkali earth metal salt with a suitable anionic salt (e.g., silver nitrate).

In an exemplary embodiment of the present invention, a compound represented by Formula 1 of the present invention was prepared and its structure was analyzed and confirmed through NMR or a mass spectrum (see Example 1).

In addition, in another aspect of the present invention, the present invention provides a pharmaceutical composition for preventing or treating cancer, which includes the compound represented by Formula 1, an isomer thereof or a pharmaceutically acceptable salt thereof as an active ingredient.

In addition, the composition of the present invention includes pharmaceutical and health functional food compositions.

The term “prevention” used herein refers to all actions of inhibiting cancer or delaying the onset thereof by administration of the pharmaceutical composition according to the present invention.

The term “treatment” used herein refers to all actions involved in alleviating or beneficially changing symptoms of cancer by administration of the pharmaceutical composition according to the present invention.

The “cancer” which is a disease to be prevented and treated by the composition of the present invention is defined as a disease in which normal tissue cells are proliferated indefinitely for some reasons and continue to grow rapidly regardless of the living state of the vital phenomenon of an organism or surrounding tissue conditions, and “cancer” includes dysplasia, hyperplasia, solid tumors and hematopoietic cancer, but the present invention is not limited thereto, and includes various cancer types known in the art. Other types of cancer may include, but are not limited to, cancer occurring in the following organs: the brain, heart, lungs, stomach, colon, genitourinary tract, liver, bones, nervous system, uterus, blood, skin, breasts and adrenal glands. Still other types of cancer cells include gliomas (schwannomas, glioblastoma, astrocytomas), neuroblastoma, pheochromocytomas, paragangliomas, meningiomas, adrenal cortical cancer, medulloblastoma, rhabdomyosarcoma, renal cancer, various types of blood vessel cancer, osteoblastic osteocarcinoma, prostate cancer, ovarian cancer, uterine fibroids (urerine leiomyomas), salivary gland cancer, choroid plexus carcinoma, breast cancer, pancreatic cancer, colon cancer, colorectal cancer and megakaryocytic leukemia; and skin cancer including malignant melanoma, basal cell carcinoma, squamous cell carcinoma, Karposi’s sarcoma, atypical moles (dysplastic nevi), lipomas, angiomas, dermatofibroma, keloids, a sarcoma such as fibrosarcoma or angiosarcoma, and melanoma.

In addition, the cancer of the present invention may be a disease resulting from overexpression of MDH1 and/or MDH2. More specifically, the MDH1 and MDH2 of the present invention are isozymes generated by different MDH genes, and MDHs are present in the cytoplasm and the mitochondrial matrix. More specifically, MDH1 and MDH2 are involved in reversible conversion between malate and oxaloacetate (OAA) using the NAD/NADH cofactor system. MDH1 present in the cytoplasm catalyzes the reduction of OAA to malate, and thus oxidation of NADH to $NAD^+$. In the malate-aspartate shuttle, malate is transferred into the mitochondria, and reoxidized to OAA by mitochondrial MDH2, thereby generating NADH. The generated NADH produces ATP through the electron transport system. In addition to this, MDH2 associated with the TCA cycle is involved in ATP production through respiration.

Accordingly, the composition of the present invention may inhibit MDH1 and/or MDH2 activity, and particularly, simultaneously inhibit MDH1 and MDH2 activities.

The term “inhibition” used herein refers to inhibition of an arbitrary step of transcription, mRNA processing, translation, translocation and maturation of a gene, or inhibition of protein-protein interactions, protein activation or signal transduction thereby.

In an exemplary embodiment of the present invention, MDH1 and MDH2 inhibitory activity according to the treatment of a compound synthesized by the preparation method of the present invention were confirmed (see Experimental Example 1). In addition, the MDH inhibition mechanism was confirmed using the compound of the present invention (see Experimental Example 2), an HIF-1α inhibitory effect was confirmed using the compound of the present invention (see Experimental Example 3), a mitochondrial respiration inhibitory effect in cancer cells was confirmed (see Experimental Example 4), an effect of reducing the weight and size of a tumor was specifically confirmed using cancer cell-transplanted mouse models (see Experimental Example 5), confirming that the compound of the present invention can be very effectively used as a pharmaceutical composition for preventing or treating cancer.

Accordingly, the compound represented by Formula 1 according to the present invention, an isomer thereof or a pharmaceutically acceptable salt thereof may be effectively used as an active ingredient of a pharmaceutical composition for preventing, improving or treating cancer.

The pharmaceutical composition of the present invention may include a pharmaceutically acceptable carrier, in addition to the active ingredient. Here, the pharmaceutically acceptable carrier may be generally used in formulation, and includes, but not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propyl hydroxybenzoate, talc, magnesium stearate and mineral oil. In addition, the pharmaceutical composition of the present invention may further include a lubricant, a wetting agent, a sweetening agent, a flavoring agent, an emulsifier, a suspending agent and a preservative, other than the above-described components.

The pharmaceutical composition of the present invention may be orally or parenterally (e.g., intravenously, subcutaneously, intraperitoneally or locally) administered according to a desired method, and a dose may vary according to the condition and body weight of a patient, the severity of a disease, a drug type, an administration route and time, and may be appropriately selected by one of ordinary skill in the art.

The pharmaceutical composition of the present invention is administered at a pharmaceutically effective amount. The “pharmaceutically effective amount” used herein refers to an amount sufficient for treating a disease at a reasonable benefit/risk ratio applicable for medical treatment, and an effective dosage may be determined by parameters including a type of a patient’s disease, severity, drug activity, sensitivity to a drug, administration time, an administration route and an excretion rate, the duration of treatment and drugs simultaneously used, and other parameters well known in medical fields. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, an effective amount of the pharmaceutical composition of the present invention may be dependent on a patient's age, sex, condition and body weight, an absorption rate of the active ingredient in the body, an inactivation rate, an excretion rate, a type of disease, or a drug used in combination, and may be generally administered at 0.001 to 150 mg, and preferably, 0.01 to 100 mg, per kg of body weight daily or every other day, or divided into one to three daily administrations. However, the effective amount may vary depending on an administration route, the severity of obesity, sex, body weight or age, and therefore, the scope of the present invention is not limited by the dose in any way.

In addition, the present invention provides a method of preventing, controlling or treating cancer, which includes administering the pharmaceutical composition to an individual. The "individual" used herein refers to a subject requiring treatment of a disease, and more specifically, a mammal such as a human, or a non-human primate, a mouse, a rat, a dog, a cat, a horse, and a cow.

Hereinafter to help in understanding the present invention, exemplary examples will be suggested. However, the following examples are merely provided to more easily understand the present invention, and not to limit the present invention.

EXAMPLES

Example 1. Synthesis of Compounds Having MDH1 and MDH2 Inhibitory Activity

As an MDH inhibitor according to the present invention, non-limiting examples of compounds used as an active ingredient of a pharmaceutical composition include the following compounds, isomers thereof and pharmaceutically acceptable salts thereof. The following compounds according to the present invention were synthesized by suitably changing reactants and/or starting materials used in a known method.

First, a process of synthesizing the following compounds according to the present invention is the same as shown in FIG. 1, and reagents and conditions used in each process are described below.

Reagents and conditions: a) (i) $K_2CO_3$, methyl-4-bromobutanoate or methyl 2-bromo-2-methylpropanoate, DMF; (ii) LiOH, $THF/H_2O$; b) EDC·HCl, HOBT, DIPEA, DMF, $NH_2$—$R_2$; c) $PPh_3$, methylpropiolate, toluene; d, g) LiOH, $THF/H_2O$; e) EDC·HCl, HOBT, DIPEA, DMF, $NH_2$—$R_2$ or HATU, DIPEA, DMF, $NH_2$—$R_2$; f) Pd/C, $H_2$, MeOH; h) EDC·HCl, HOBT, DIPEA, DMF, $NH_2$—$R_2$ or HATU, DIPEA, DMF/THF, $NH_2$—$R_2$ or i) CDI, THF; ii) $NH_2$—$R_2$, imidazole, THF.

In addition, specific synthesis processes for the compounds obtained as an MDH inhibitor according to the present invention, their yields and NMR measurement results are described below.

1-1. Synthesis of Compounds 3-1 to 3-34

As shown in FIG. 1, Compounds 3-1 to 3-34 were synthesized using Compound 1 as a starting material and Compound 2 as an intermediate.

First, a process of synthesizing Compound 2 is as follows.

Process of synthesizing Compound 2: A mixture of Compound 1 (1.0 equiv), anhydrous potassium carbonate (2.0 equiv) and methyl 4-bromobutanoate or methyl α-bromoisobutyrate (2.0 equiv) was stirred in dimethylformamide (DMF) overnight under a room temperature condition. The reaction mixture was diluted with EtOAc, and successively, washed with water-soluble sodium bicarbonate, brine and water. An organic layer was collected, and dehydrated with anhydrous $MgSO_4$. The solvent was filtered and evaporated under a reduced pressure condition, such that a crude dry product purified by silica gel column chromatography became an ester compound. An ester compound suspension (1.0 equiv) in $THF/H_2O$ (1:1) was added to lithium hydroxide monohydrate (3.0 equiv), and stirred overnight at room temperature. The reaction mixture was neutralized with 10% HCl, diluted with EtOAc, and successively washed with water-soluble sodium bicarbonate, brine and water. An organic layer was collected, and then dehydrated with anhydrous $MgSO_4$. The solvent was filtered and evaporated under a reduced pressure condition, thereby obtaining a crude dry product purified by silica gel column chromatography.

Compound 3-1: Methyl 3-(2-(4-nitrophenoxy)acetamido)benzoate 2-(4-nitrophenoxy)acetic acid (1.0 equiv) and methyl 3-aminobenzoate (1.0 equiv) were mixed in DMF, and the resulting mixture was added to N-(3-dimethylaminopropyl)-N'-ethylcarbonate hydrochloride (EDC·HCl) (1.2 equiv), 1-hydroxybenzotriazole (HOBT) (1.2 equiv) and N,N-diisopropylethylamine (DIPEA) (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-nitrophenoxy)acetamido)benzoate (white solid, 0.21 g, 64.2% yield).

$^1$H-NMR (400 MHz, DMSO) δ 10.5 (brs, 1H), 8.33 (t, J=1.8 Hz, 1H), 8.25 (d, J=9.4 Hz, 2H), 7.89 (m, 1H), 7.69 (d, J=7.8 Hz, 1H), 7.50 (t, J=8.0 Hz, 1H), 7.23 (d, J=9.0 Hz, 2H), 4.95 (s, 2H), 3.86 (s, 3H); $^{13}$C-NMR (100 MHz, DMSO) δ 166.4, 163.5, 141.7, 139.1, 130.6, 129.7, 126.3, 124.8, 124.5, 120.5, 115.7, 67.6, 52.7; HRMS [M+H] calcd [$C_{16}H_{15}N_2O_6$]: 329.0852, Found: 329.0676; Purity: 97.3% (as determined by RP-HPLC, method A, tR=14.62 min).

Compound 3-2: Methyl 3-(2-(4-(trifluoromethyl)phenoxy)acetamido)benzoate 2-(4-(trifluoromethyl)phenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-(trifluoromethyl)phenoxy)acetamido)benzoate (white solid, 0.01 g, 40.8% yield).

$^1$H-NMR (400 MHz, $CDCl_3$) δ 8.32 (s, 1H), 8.07 (s, 1H), 8.01 (d, J=8.0 Hz, 1H), 7.85 (d, J=7.2 Hz, 1H), 7.64 (d, J=8.4 Hz, 2H), 7.46 (t, J=7.8 Hz, 1H), 7.09 (d, J=8.4 Hz, 2H), 4.68 (s, 2H), 3.93 (s, 3H), 1.62 (s, 2H); $^{13}$C-NMR (100 MHz, $CDCl_3$) δ 166.5, 159.1, 136.8, 131.0, 129.4, 127.5, 127.4, 127.4, 126.1, 124.6, 120.9, 114.9, 67.4, 52.3; HRMS [M+H] calcd [$C_{17}H_{15}F_3NO_4$]: 354.0875, Found: 354.0929; Purity: 99.99% (as determined by RP-HPLC, method A, tR=17.70 min).

Compound 3-3: Methyl 3-(2-(4-tert-butylphenoxy)acetamido)benzoate 2-(4-tert-butylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-tert-butylphenoxy)acetamido)benzoate (white solid, 0.11 g, 61.3% yield).

$^1$H-NMR (400 MHz, $CDCl_3$) δ 8.40 (s, 1H), 8.07 (s, 1H), 8.01 (d, J=8.0 Hz, 1H), 7.83 (d, J=8.0 Hz, 1H), 7.47 (t, J=12.0 Hz, 1H), 7.36 (d, J=8.0 Hz, 2H), 6.93 (d, J=8.0 Hz, 2H), 4.61 (s, 2H), 3.92 (s, 3H), 1.31 (s, 9H); $^{13}$C-NMR (100 MHz, $CDCl_3$) δ 166.7, 166.6, 154.8, 145.5, 137.1, 131.1, 129.3, 126.8, 125.9, 124.5, 120.9, 114.4, 67.8, 52.3, 34.2, 31.5; HRMS [M+H] calcd [$C_{20}H_{24}NO_4$]: 342.1705, Found: 342.1705; Purity: 100% (as determined by RP-HPLC, method A, tR=18.66 min).

Compound 3-4: Methyl 3-(2-(p-tolyloxy)acetamido)benzoate 2-(p-tolyloxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(p-tolyloxy)acetamido)benzoate (white solid, 0.10 g, 40.4% yield).

$^1$H-NMR (400 MHz, $CDCl_3$) δ 8.51 (s, 1H), 8.09 (t, J=8.0 Hz, 1H), 7.99 (m, 1H), 7.80 (d, J=7.4 Hz, 1H), 7.40 (t, J=8.0 Hz, 1H), 7.12 (d, J=8.2 Hz, 2H), 6.87 (m, 2H), 4.56 (s, 2H), 3.89 (s, 3H), 2.29 (s, 3H); $^{13}$C-NMR (100 MHz, $CDCl_3$) δ 166.7, 166.5, 154.9, 137.2, 131.8, 130.9, 130.3, 129.2, 125.8, 124.5, 120.9, 114.6, 67.7, 52.3, 20.5; HRMS [M+H] calcd [$C_{17}H_{18}NO_4$]: 300.1158, Found: 300.1232; Purity: 100% (as determined by RP-HPLC, method A, tR=16.29 min).

Compound 3-5: Methyl 3-(2-(4-ethylphenoxy)acetamido)benzoate 2-(4-ethylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-ethylphenoxy)acetamido)benzoate (white solid, 0.34 g, 97.2% yield).

$^1$H-NMR (400 MHz, $CDCl_3$) δ 8.48 (brs, 1H), 8.00 (m, 1H), 7.81 (m, 1H), 7.42 (t, J=7.8 Hz, 1H), 7.16 (d, J=8.0 Hz, 2H), 6.91 (m, 2H), 4.59 (s, 2H), 3.90 (s, 3H), 2.61 (q, J=7.4 Hz, 2H), 1.23 (m, 3H); $^{13}$C-NMR (100 MHz, $CDCl_3$) δ 166.7, 166.5, 155.0, 138.3, 137.1, 13.9, 129.2, 129.1, 125.8, 124.5, 120.9, 114.7, 67.7, 52.2, 28.0, 15.8; HRMS [M+H] calcd [$C_{18}H_{20}NO_4$]: 314.1314, Found: 314.1379; Purity: 100% (as determined by RP-HPLC, method A, tR=18.06 min).

Compound 3-6: Methyl 3-(2-(4-propylphenoxy)acetamido)benzoate 2-(4-propylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-propylphenoxy)acetamido)benzoate (white solid, 0.31 g, 90.5% yield).

$^1$H-NMR (400 MHz, $CDCl_3$) δ 8.46 (brs, 1H), 8.09 (t, J=1.8 Hz, 1H), 8.00 (dd, J=8.2 Hz, 1H), 7.82 (dd, J=7.8 Hz, 1H), 7.42 (t, J=8.0 Hz, 1H), 7.14 (d, J=8.6 Hz, 2H), 6.90 (m, 2H), 4.59 (s, 2H), 3.91 (s, 3H), 2.54 (m, 2H), 1.61 (m, 2H), 0.93 (t, J=7.2 Hz, 3H); $^{13}$C-NMR (100 MHz, $CDCl_3$) δ 166.7, 166.6, 155.0, 137.1, 136.8, 131.0, 129.7, 129.2, 125.8, 124.5, 120.9, 114.6, 67.7, 52.3, 37.1, 24.7, 13.7; HRMS [M+H] calcd [$C_{19}H_{22}NO_4$]: 328.2471, Found: 328.1546; Purity: 100% (as determined by RP-HPLC, method A, tR=19.92 min).

Compound 3-7: Methyl 3-(2-(4-butylphenoxy)acetamido)benzoate 2-(4-butylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-butylphenoxy)acetamido)benzoate (white solid, 0.32 g, 98.4% yield).

$^1$H-NMR (400 MHz, $CDCl_3$) δ 8.52 (brs, 1H), 8.10 (s, 1H), 7.99 (dd, J=8.2, 1.2 Hz, 1H), 7.80 (d, J=7.8 Hz, 1H), 7.40 (t, J=7.8 Hz, 1H), 7.13 (d, J=8.6 Hz, 2H), 6.89 (d, J=8.6 Hz, 2H), 4.57 (s, 2H), 3.89 (s, 3H), 2.56 (t, J=7.6 Hz, 2H), 1.56 (m, 2H), 1.34 (m, 2H), 0.92 (t, J=7.4 Hz, 3H); $^{13}$C-NMR (100 MHz, $CDCl_3$) δ 166.8, 166.5, 155.0, 137.2, 137.0, 130.9, 129.6, 129.2, 125.8, 124.5, 120.9, 114.6, 67.7, 52.2, 34.7, 33.8, 22.3, 14.0; HRMS [M+H] calcd $[C_{20}H_{24}NO_4]$: 342.1627, Found: 342.1694; Purity: 100% (as determined by RP-HPLC, method A, tR=21.59 min).

Compound 3-8: Methyl 3-(2-(4-pentylphenoxy)acetamido)benzoate 2-(4-pentylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-pentylphenoxy)acetamido)benzoate (yellow solid, 0.13 g, 81.2% yield).

$^1$H-NMR (400 MHz, $CDCl_3$) δ 8.40 (s, 1H), 8.07 (s, 1H), 8.01 (d, J=8.0 Hz, 1H), 7.82 (d, J=8.0 Hz, 1H), 7.44 (t, J=12.0 Hz, 1H), 7.15 (d, J=8.0 Hz, 2H), 6.91 (d, J=8.0 Hz, 2H), 4.60 (s, 2H), 3.92 (s, 3H), 2.56 (t, J=8.0 Hz, 2H), 1.61-1.57 (m, 2H), 1.34-1.29 (m, 4H), 0.89 (t, J=4.0 Hz, 1H); $^{13}$C-NMR (100 MHz, $CDCl_3$) δ 166.7, 166.6, 155.0, 137.2, 137.1, 131.1, 129.7, 129.3, 125.9, 124.5, 120.9, 114.7, 67.8, 52.3, 35.0, 31.4, 31.3, 22.5, 14.0; HRMS [M+H] calcd $[C_{21}H_{26}NO_4]$: 356.1862, Found: 356.1862; Purity: 100% (as determined by RP-HPLC, method A, tR=23.53 min).

Compound 3-9: Methyl 3-(2-(4-cyclopentylphenoxy)acetamido)benzoate 2-(4-cyclopentylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-cyclopentylphenoxy)acetamido)benzoate (yellow solid, 0.10 g, 62.5% yield).

$^1$H-NMR (400 MHz, $CDCl_3$) δ 8.39 (s, 1H), 8.07 (s, 1H), 8.01 (d, J=8.0 Hz, 1H), 7.83 (d, J=8.0 Hz, 1H), 7.45 (t, J=12.0 Hz, 1H), 7.22 (d, J=8.0 Hz, 2H), 6.92 (d, J=8.0 Hz, 2H), 4.61 (s, 2H), 3.93 (s, 3H), 2.98-2.94 (m, 1H), 2.06-2.05 (m, 2H), 1.82-1.77 (m, 2H), 1.70-1.67 (m, 2H), 1.57-1.52 (m, 4H); $^{13}$C-NMR (100 MHz, $CDCl_3$) (166.7, 166.6, 155.1, 140.8, 137.1, 131.1, 129.3, 128.4, 125.9, 124.5, 120.9, 114.7, 67.9, 52.3, 45.2, 34.7, 25.4; HRMS [M+H] calcd $[C_{21}H_{24}NO_4]$: 354.1705, Found: 354.1705; Purity: 100% (as determined by RP-HPLC, method A, tR=22.03 min).

Compound 3-10: Methyl 3-(2-(4-cyclohexylphenoxy)acetamido)benzoate 2-(4-cyclohexylphenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-cyclohexylphenoxy)acetamido)benzoate (yellow solid, 0.11 g, 70.5% yield).

$^1$H-NMR (400 MHz, $CDCl_3$) 8.39 (s, 1H), 8.07 (s, 1H), 8.00 (d, J=8.0 Hz, 1H), 7.82 (d, J=8.0 Hz, 1H), 7.45 (t, J=12.0 Hz, 1H), 7.19 (d, J=8.0 Hz, 2H), 6.92 (d, J=8.0 Hz, 2H), 4.60 (s, 2H), 3.92 (s, 3H), 2.50-2.46 (m, 1H), 1.84-1.76 (m, 4H), 1.73-1.58 (m, 2H), 1.44 (m, 4H); $^{13}$C-NMR (100 MHz, $CDCl_3$) δ 166.7, 166.6, 155.1, 142.4, 137.1, 131.1, 129.3, 128.1, 125.9, 124.5, 120.9, 114.7, 67.8, 52.3, 43.3, 34.6, 26.9, 26.1; HRMS [M+H] calcd $[C_{22}H_{26}NO_4]$: 368.1862, Found: 368.1862; Purity: 100% (as determined by RP-HPLC, method A, tR=23.62 min).

Compound 3-11: Methyl 3-(2-(4-(2,4,4-trimethylpentan-2-yl)phenoxy)acetamido)benzoate 2-(4-(2,4,4-trimethylpentan-2-yl)phenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-(2,4,4-trimethylpentan-2-yl)phenoxy)acetamido)benzoate (white solid, 0.10 g, 64.1% yield).

$^1$H-NMR (400 MHz, $CDCl_3$) δ 8.46 (s, 1H), 8.08 (s, 1H), 7.79 (d, J=8.0 Hz, 1H), 7.81 (d, J=8.0 Hz, 1H), 7.44-7.32 (m, 1H), 7.33 (d, J=8.0 Hz, 2H), 6.90 (d, J=8.0 Hz, 2H), 4.60 (s, 2H), 3.91 (s, 3H) 1.71 (s, 2H), 1.35 (s, 6H), 0.71 (s, 9H); $^{13}$C-NMR (100 MHz, $CDCl_3$) δ 166.7, 166.6, 154.6, 144.3, 137.1, 131.0, 129.3, 127.5, 125.8, 124.5, 120.9, 114.0, 67.6, 56.9, 52.3, 30.1, 32.3, 31.8, 31.6; HRMS [M+H] calcd $[C_{24}H_{32}NO_4]$: 398.2331, Found: 398.2331; Purity: 100% (as determined by RP-HPLC, method A, tR=26.11 min).

Compound 3-12: Methyl 4-hydroxy-3-(2-(4-(2,4,4-trimethylpentan-2-yl)phenoxy)acetamido)benzoate 2-(4-(2,4,4-trimethylpentan-2-yl)phenoxy)acetic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 4-hydroxy-3-(2-(4-(2,4,4-trimethylpentan-2-yl)phenoxy)acetamido)benzoate (white solid, 1.00 g, 64.1% yield).

$^1$H-NMR (400 MHz, $CDCl_3$) δ 9.75 (s, 1H), 8.60 (s, 1H), 7.85-7.83 (m, 1H), 7.73 (s, 1H), 7.38-7.34 (m, 2H), 7.06 (d, J=8.0 Hz, 1H), 6.94-6.90 (m, 2H), 4.68 (s, 2H), 3.89 (s, 3H), 1.73 (s, 2H), 1.36 (s, 6H), 0.72 (s, 9H); $^{13}$C-NMR (100 MHz, $CDCl_3$) δ 168.2, 166.7, 154.5, 147.2, 144.6, 129.2, 128.0, 127.6, 122.3, 121.3, 119.5, 114.2, 67.5, 57.0, 52.3, 38.1, 32.3, 31.8, 31.6; HRMS [M+H] calcd $[C_{24}H_{32}NO_5]$:

414.2280, Found: 414.2280; Purity: 100% (as determined by RP-HPLC, method A, tR=24.95 min).

Compound 3-13: N-(4-(trifluoromethyl)phenyl)-2-(4-(2,4,4-trimethylpentan-2-yl)phenoxy)acetamide 2-(4-(2,4,4-trimethylpentan-2-yl)phenoxy)acetic acid (1.0 equiv) and 4-(trifluoromethyl)aniline (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining N-(4-(trifluoromethyl)phenyl)-2-(4-(2,4,4-trimethylpentan-2-yl)phenoxy)acetamide (white solid, 0.11 g, 71.5% yield).

$^1$H-NMR (400 MHz, $CDCl_3$) δ 8.43 (s, 1H), 7.72 (d, J=8.8 Hz, 2H), 7.61 (d, J=8.8 Hz, 2H), 7.35 (d, J=6.4 Hz, 2H), 6.91 (d, J=6.8 Hz, 2H), 4.62 (s, 2H), 1.72 (s, 2H), 1.36 (s, 6H), 0.71 (s, 9H); $^{13}$C-NMR (100 MHz, $CDCl_3$) δ 166.8, 154.5, 144.5, 139.9, 127.6, 126.8, 126.4, 126.3, 120.0, 114.1, 67.6, 56.9, 38.1, 32.3, 31.8, 31.6; HRMS [M+H] calcd [$C_{23}H_{29}F_3NO_2$]: 408.2150, Found: 408.2150; Purity: 100% (as determined by RP-HPLC, method A, tR=28.40 min).

Compound 3-14: N-(4-(4-methylpiperazin-1-yl)phenyl)-2-(4-(2,4,4-trimethylpentan-2-yl)phenoxy)acetamide 2-(4-(2,4,4-trimethylpentan-2-yl)phenoxy)acetic acid (1.0 equiv) and 4-(4-methylpiperazin-1-yl)aniline (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining N-(4-(4-methylpiperazin-1-yl)phenyl)-2-(4-(2,4,4-trimethylpentan-2-yl)phenoxy)acetamide (white solid, 0.12 g, 72.7% yield).

$^1$H-NMR (400 MHz, $CDCl_3$) δ 8.17 (s, 1H), 7.45 (d, J=9.2 Hz, 2H), 7.33 (d, J=8.8 Hz, 2H), 6.92-6.88 (m, 4H), 4.58 (s, 2H), 3.25-3.23 (m, 4H), 2.68-2.67 (m, 4H), 2.42 (s, 3H), 1.71 (s, 2H), 1.31 (s, 6H), 0.71 (s, 9H); $^{13}$C-NMR (100 MHz, $CDCl_3$) δ 166.2, 154.7, 148.7, 144.1, 129.2, 127.5, 121.6, 116.6, 114.0, 67.7, 57.0, 55.1, 49.4, 46.1, 38.1, 32.3, 31.8, 31.6; HRMS [M+H] calcd [$C_{27}H_{40}N_3O_2$]: 438.3121, Found: 438.3121; Purity: 100% (as determined by RP-HPLC, method A, tR=12.56 min).

Compound 3-15: 1-(4-(4-(trifluoromethyl)benzyl)piperazin-1-yl)-2-(4-(2,4,4-trimethylpentan-2-yl)phenoxy)ethanone 2-(4-(2,4,4-trimethylpentan-2-yl)phenoxy)acetic acid (1.0 equiv) and 1-(4-(trifluoromethyl)benzyl)piperazine (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining 1-(4-(4-(trifluoromethyl)benzyl)piperazin-1-yl)-2-(4-(2,4,4-trimethylpentan-2-yl)phenoxy)ethanone (white solid, 0.15 g, 81.0% yield).

$^1$H-NMR (400 MHz, $CDCl_3$) δ 7.58 (d, J=7.6 Hz, 2H), 7.43 (d, J=7.6 Hz, 2H), 7.27 (d, J=8.0 Hz, 2H), 6.85 (d, J=8.8 Hz, 2H), 4.66 (s, 2H), 3.63-3.59 (m, 4H), 3.56 (s, 2H), 2.40-2.39 (m, 4H), 1.70 (s, 2H), 1.38 (s, 6H), 0.71 (s, 9H); $^{13}$C-NMR (100 MHz, $CDCl_3$) δ 166.6, 155.4, 143.2, 142.0, 129.4, 129.1, 127.2, 125.3, 125.2, 113.8, 67.9, 62.2, 57.0, 53.2, 52.7, 45.4, 42.1, 38.0, 32.3, 31.8, 31.6; HRMS [M+H] calcd [$C_{28}H_{38}F_3N_2O_2$]: 491.2885, Found: 491.2885; Purity: 100% (as determined by RP-HPLC, method A, tR=14.31 min).

Compound 3-16: 1-(4-(prop-2-ynyl)piperazin-1-yl)-2-(4-(2,4,4-trimethylpentan-2-yl)phenoxy)ethanone 2-(4-(2,4,4-trimethylpentan-2-yl)phenoxy)acetic acid (1.0 equiv) and 1-(prop-2-ynyl)piperazine (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining 1-(4-(prop-2-ynyl)piperazin-1-yl)-2-(4-(2,4,4-trimethylpentan-2-yl)phenoxy)ethanone (white solid, 0.11 g, 78.5% yield).

$^1$H-NMR (400 MHz, $CDCl_3$) δ 7.30 (d, J=8.0 Hz, 2H), 6.85 (d, J=8.0 Hz, 2H), 4.67 (s, 2H), 3.68-3.63 (m, 4H), 3.29 (t, J=4.0 Hz, 2H), 2.56-2.51 (m, 4H), 2.25 (t, J=4.0 Hz, 1H), 1.69 (s, 2H), 1.33 (s, 6H), 0.70 (s, 9H); $^{13}$C-NMR (100 MHz, $CDCl_3$) δ 166.6, 155.4, 143.3, 127.2, 113.8, 78.1, 73.6, 67.9, 57.0, 51.9, 51.6, 46.8, 45.2, 41.9, 38.0, 32.3, 31.8, 31.6; HRMS [M+H] calcd [$C_{23}H_{35}N_2O_2$]: 371.2699, Found: 371.2699; Purity: 100% (as determined by RP-HPLC, method A, tR=11.38 min).

Compound 3-17: Prop-2-ynyl 4-hydroxy-3-(2-(4-(2,4,4-trimethylpentan-2-yl)phenoxy)acetamido)benzoate 2-(4-(2,4,4-trimethylpentan-2-yl)phenoxy)acetic acid (1.0 equiv) and prop-2-ynyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining prop-2-ynyl 4-hydroxy-3-(2-(4-(2,4,4-trimethylpentan-2-yl)phenoxy)acetamido)benzoate (white solid, 0.10 g, 60.6% yield).

$^1$H-NMR (400 MHz, $CDCl_3$) δ 9.84 (s, 1H), 8.63 (s, 1H), 7.88 (d, J=8.0 Hz, 1H), 7.76 (d, J=4.0 Hz, 1H), 7.36 (d, J=8.0 Hz, 2H), 7.07 (d, J=8.0 Hz, 1H), 6.92 (d, J=8.0 Hz, 2H), 4.91 (d, J=4.0 Hz, 2H), 4.69 (s, 2H), 2.51 (t, J=4.0 Hz, 1H), 1.72 (s, 2H), 1.36 (s, 6H), 0.72 (s, 9H); $^{13}$C-NMR (100 MHz, $CDCl_3$) δ 169.0, 164.9, 154.2, 153.7, 144.8, 129.6, 127.7, 124.6, 124.5, 121.6, 120.2, 114.1, 77.7, 75.1, 67.1, 56.9, 52.4, 38.1, 32.3, 31.8, 31.6; HRMS [M+H] calcd [$C_{26}H_{32}NO_5$]: 438.2280, Found: 438.2280; Purity: 100% (as determined by RP-HPLC, method A, tR=24.56 min).

Compound 3-18: N-(3-hydroxy-adamantan-1-yl)-2-(4-(2,4,4-trimethylpentan-2-yl)phenoxy)acetamide 2-(4-(2,4,4-trimethylpentan-2-yl)phenoxy)acetic acid (1.0 equiv) and 3-hydroxy-adamantan-1-yl-amine (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining N-(3-hydroxy-admantan-1-yl)-2-(4-(2,4,4-trimethylpentan-2-yl)phenoxy)acetamide (white solid, 0.12 g, 76.9% yield).

$^1$H-NMR (400 MHz, $CDCl_3$) δ 8.02 (s, 1H), 7.31 (d, J=4.0 Hz, 2H), 6.81 (d, J=12.0 Hz, 2H), 6.31 (s, 1H), 4.36 (s, 2H), 2.28 (s, 2H), 2.02 (s, 2H), 1.99 (s, 4H), 1.70 (s, 6H), 1.58 (s, 2H), 1.34 (s, 6H), 0.70 (s, 9H); $^{13}$C-NMR (100 MHz, $CDCl_3$) δ 167.4, 154.7, 143.7, 127.4, 113.9, 69.0, 67.6, 57.0, 54.2, 48.9, 44.0, 40.2, 38.0, 34.8, 32.3, 31.7, 31.6, 30.6; HRMS [M+H] calcd [$C_{26}H_{40}NO_3$]: 414.3008, Found: 414.3008; Purity: 100% (as determined by RP-HPLC, method A, tR=23.33 min).

Compound 3-19: Methyl 3-(2-(4-adamantan-1-yl-phenoxy)acetamido)benzoate (4-adamantan-1-yl-phenoxy)acetic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)acetamido)benzoate (white solid, 0.12 g, 82.2% yield).

$^1$H-NMR (400 MHz, $CDCl_3$) δ 8.40 (s, 1H), 8.07 (s, 1H), 8.00 (d, J=8.0 Hz, 1H), 7.82 (d, J=8.0 Hz, 1H), 7.43 (t, J=8.0 Hz, 1H), 7.33 (d, J=8.0 Hz, 2H), 6.95 (d, J=8.0 Hz, 1H), 4.61 (s, 2H), 3.92 (s, 3H), 2.09 (brs, 3H), 1.82-1.81 (m, 6H), 1.77-1.72 (m, 6H); $^{13}$C-NMR (100 MHz, $CDCl_3$) δ 166.7, 166.6, 154.8, 145.8, 137.1, 131.1, 129.3, 126.3, 125.9, 124.5, 120.9, 114.4, 67.8, 52.3, 43.3, 36.8, 35.7, 29.0; HRMS [M+H] calcd [$C_{26}H_{30}NO_4$]: 420.2175, Found: 420.2175; Purity: 100% (as determined by RP-HPLC, method A, tR=26.99 min).

Compound 3-20: Methyl 3-(2-(4-adamantan-1-yl-phenoxy)acetamido)-4-hydroxybenzoate 2-(4-(adamantan-1-yl)phenoxy)acetic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)acetamido)-4-hydroxybenzoate.

$^1$H-NMR (300 MHz, DMSO) δ 11.10 (s, 1H), 9.24 (s, 1H), 8.69 (m, 1H), 7.60-7.64 (m, 1H), 7.30 (d, J=8.4 Hz, 2H), 6.94-6.99 (m, 3H), 4.74 (s, 2H), 3.79 (s, 3H), 2.04 (m, 3H), 1.83 (m, 6H), 1.72 (m, 6H); MS (ESI) m/z 434 $(M-H)^-$; HRMS (ESI) m/z calcd for $C_{26}H_{29}O_5NNa$ [$(M+Na)^+$]: 458.1943, Found: 458.1942.

Compound 3-21: Methyl 3-(2-(4-adamantan-1-yl-phenoxy)acetamido)-4-(2-ethoxy-2-oxoethoxy)benzoate Methyl 3-(2-(4-adamantan-1-yl-phenoxy)acetamido)-4-hydroxybenzoate (1.0 equiv), anhydrous potassium carbonate (3.0 equiv) and ethyl chloroacetate (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)acetamido)-4-(2-ethoxy-2-oxoethoxy)benzoate (white solid, 0.09 g, 75.0% yield).

$^1$H-NMR (400 MHz, $CDCl_3$) δ 9.27 (s, 1H), 9.06 (s, 1H), 7.81 (d, J=8.0 Hz, 1H), 7.32 (d, J=8.0 Hz, 2H), 7.01 (d, J=8.0 Hz, 2H), 6.84 (d, J=8.0 Hz, 1H), 4.71 (s, 2H), 4.64 (s, 2H), 4.28 (q, J=8.0 Hz, 2H), 3.90 (s, 3H), 2.09 (brs, 3H), 1.89-1.88 (m, 6H), 1.77-1.75 (m, 6H), 1.28 (t, J=12.0 Hz, 3H); $^{13}$C-NMR (100 MHz, $CDCl_3$) δ 166.7, 166.7, 155.0, 150.3, 145.4, 127.3, 126.6, 126.1, 124.4, 121.7, 114.5, 111.3, 67.8, 66.2, 61.8, 52.1, 43.3, 36.7, 35.7, 28.9, 14.2; HRMS [M+H] calcd [$C_{30}H_{36}NO_7$]: 522.2492, Found: 522.2492; Purity: >96.0% (as determined by RP-HPLC, method A, tR=28.66 min).

Compound 3-22: Methyl 3-(2-(4-adamantan-1-yl-phenoxy)acetamido)-4-(2-(pyrrolidin-1-yl)ethoxy)benzoate Methyl 3-(2-(4-adamantan-1-yl-phenoxy)acetamido)-4-hydroxybenzoate (1.0 equiv), anhydrous potassium carbonate (3.0 equiv) and 1-(2-chloroethyl)pyrrolidine (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)acetamido)-4-(2-(pyrrolidin-1-yl)ethoxy)benzoate (white solid, 0.09 g, 75.0% yield).

$^1$H-NMR (400 MHz, $CDCl_3$) δ 9.06 (s, 1H), 9.02 (s, 1H), 7.82 (d, J=8.0 Hz, 1H), 7.32 (d, J=8.0 Hz, 2H), 6.95-6.91 (m, 3H), 4.62 (s, 2H), 4.22 (t, J=4.0 Hz, 2H), 3.89 (s, 3H), 2.92 (t, J=4.0 Hz, 2H), 2.64-2.62 (m, 4H), 2.09 (brs, 3H), 1.89-1.88 (m, 6H), 1.77-1.72 (m, 10H); $^{13}$C-NMR (100 MHz, $CDCl_3$) δ 114.4, 110.6, 68.3, 68.0, 54.8, 54.7, 52.0, 43.4, 36.7, 35.7, 28.9, 23.6; HRMS [M+H] calcd $[C_{32}H_{41}N_2O_5]$: 533.3015, Found: 533.3015; Purity: 100% (as determined by RP-HPLC, method A, tR=13.39 min).

Compound 3-23: Methyl 3-(2-(4-adamantan-1-yl-phenoxy)acetamido)-4-(3-morpholinopropoxy)benzoate Methyl 3-(2-(4-adamantan-1-yl-phenoxy)acetamido)-4-hydroxybenzoate (1.0 equiv), anhydrous potassium carbonate (3.0 equiv) and 4-(3-chloropropyl)morpholine (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)acetamido)-4-(3-morpholinopropoxy) benzoate (white solid, 0.09 g, 69.7% yield).

$^1$H-NMR (400 MHz, $CDCl_3$) δ 9.05 (s, 1H), 9.04 (s, 1H), 7.82 (d, J=8.0 Hz, 1H), 7.32 (d, J=8.0 Hz, 2H), 6.94-6.92 (m, 3H), 4.62 (s, 2H), 4.16 (t, J=4.0 Hz, 2H), 3.90 (s, 3H), 3.69-3.68 (m, 4H), 2.53 (t, J=4.0 Hz, 2H), 2.42-2.40 (m, 4H), 2.09 (brs, 3H), 2.02 (t, J=4.0 Hz, 2H), 1.89-1.88 (m, 6H), 1.77-1.72 (m, 6H); $^{13}$C-NMR (100 MHz, $CDCl_3$) δ 166.8, 166.3, 154.9, 151.1, 145.7, 126.7, 126.5, 126.3, 123.0, 120.9, 114.4, 110.3, 68.0, 66.9, 55.2, 53.7, 52.0, 43.4, 36.7, 35.7, 28.9; HRMS [M+H] calcd $[C_{33}H_{43}N_2O_6]$: 563.3121, Found: 563.3121; Purity: 100% (as determined by RP-HPLC, method A, tR=13.38 min).

Compound 3-24: Methyl 4-methoxy-3-(2-(4-(2,4,4-trimethylpentan-2-yl)phenoxy)acetamido)benzoate Methyl 4-hydroxy-3-(2-(4-(2,4,4-trimethylpentan-2-yl) phenoxy)acetamido)benzoate (1.0 equiv), anhydrous potassium carbonate (3.0 equiv) and methyl iodide (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 4-methoxy-3-(2-(4-(2,4,4-trimethylpentan-2-yl)phenoxy)acetamido)benzoate (white solid, 0.08 g, 77.6% yield).

$^1$H-NMR (400 MHz, $CDCl_3$) δ 9.03 (s, 1H), 8.97 (s, 1H), 7.85-7.83 (m, 1H), 7.33 (d, J=8.0 Hz, 2H), 6.93-6.90 (m, 3H), 4.63 (s, 2H), 3.93 (s, 3H), 3.89 (s, 3H), 1.71 (s, 2H), 1.35 (s, 6H), 0.71 (s, 9H); $^{13}$C-NMR (100 MHz, $CDCl_3$) δ 166.7, 166.5, 154.8, 151.9, 144.1, 127.5, 126.8, 126.5, 123.1, 121.1, 114.1, 109.6, 67.9, 56.9, 56.1, 52.0, 38.1, 32.3, 31.8, 31.7; HRMS [M+H] calcd $[C_{25}H_{34}NO_5]$: 428.2437, Found: 428.2437; Purity: 100% (as determined by RP-HPLC, method A, tR=27.91 min).

Compound 3-25: Methyl 4-(2-methoxyethoxy)-3-(2-(4-(2,4,4-trimethylpentan-2-yl)phenoxy)acetamido) benzoate Methyl 4-hydroxy-3-(2-(4-(2,4,4-trimethylpentan-2-yl) phenoxy)acetamido)benzoate (1.0 equiv), anhydrous potassium carbonate (3.0 equiv) and 1-chloro-2-methoxyethane (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 4-(2-methoxyethoxy)-3-(2-(4-(2,4,4-trimethylpentan-2-yl)phenoxy)acetamido)benzoate (white solid, 0.10 g, 87.7% yield).

$^1$H-NMR (400 MHz, $CDCl_3$) δ 9.15 (s, 1H), 9.06 (s, 1H), 7.83-7.80 (m, 1H), 7.32 (d, J=8.0 Hz, 2H), 6.94-6.90 (m, 3H), 4.62 (s, 2H), 4.23 (t, J=4.0 Hz, 2H), 3.89 (s, 3H), 3.78 (t, J=4.0 Hz, 2H), 3.44 (s, 3H), 1.71 (s, 2H), 1.34 (s, 6H), 0.70 (s, 9H); $^{13}$C-NMR (100 MHz, $CDCl_3$) δ 166.7, 166.4, 154.8, 151.0, 144.0, 127.4, 126.9, 126.6, 123.4, 121.0, 114.0, 110.7, 70.7, 68.4, 67.0, 59.2, 57.0, 52.0, 38.1, 32.3, 31.8, 31.6; HRMS [M+H] calcd $[C_{27}H_{38}NO_6]$: 472.2699, Found: 472.2699; Purity: 100% (as determined by RP-HPLC, method A, tR=27.57 min).

Compound 3-26: Methyl 4-(2-morpholinoethoxy)-3-(2-(4-(2,4,4-trimethylpentan-2-yl)phenoxy)acetamido)benzoate Methyl 4-hydroxy-3-(2-(4-(2,4,4-trimethylpentan-2-yl) phenoxy)acetamido)benzoate (1.0 equiv), anhydrous potassium carbonate (3.0 equiv) and 4-(2-chloroethyl)morpholine (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 4-(2-morpholinoethoxy)-3-(2-(4-(2,4,4-trimethylpentan-2-yl)phenoxy)acetamido)benzoate (white solid, 0.09 g, 70.8% yield).

$^1$H-NMR (400 MHz, $CDCl_3$) δ 9.06 (s, 1H), 9.04 (s, 1H), 7.84-7.81 (m, 1H), 7.32 (d, J=8.0 Hz, 2H), 6.93-6.88 (m, 3H), 4.62 (s, 2H), 4.21 (t, J=4.0 Hz, 2H), 3.90 (s, 3H), 3.69-3.66 (m, 4H), 2.83 (t, J=4.0 Hz, 2H), 2.56-2.54 (m, 4H), 1.71 (s, 2H), 1.34 (s, 6H), 0.71 (s, 9H); $^{13}$C-NMR (100 MHz, $CDCl_3$) δ 166.7, 166.4, 154.8, 151.0, 144.3, 127.5, 126.7, 123.3, 121.1, 114.1, 110.6, 68.1, 66.9, 66.8, 57.5, 56.9, 54.0, 52.1, 38.1, 32.3, 31.8, 31.6; HRMS [M+H] calcd $[C_{30}H_{43}N_2O_6]$: 527.3121, Found: 527.3121; Purity: 100% (as determined by RP-HPLC, method A, tR=12.9 min).

Compound 3-27: Methyl 4-(prop-2-ynyloxy)-3-(2-(4-(2,4,4-trimethylpentan-2-yl)phenoxy)acetamido) benzoate Methyl 4-hydroxy-3-(2-(4-(2,4,4-trimethylpentan-2-yl) phenoxy)acetamido)benzoate (1.0 equiv), anhydrous potassium carbonate (3.0 equiv) and propargyl bromide (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 4-(prop-2-ynyloxy)-3-(2-(4-(2,4,4-trimethylpentan-2-yl)phenoxy)acetamido)benzoate (white solid, 0.10 g, 91.7% yield).

$^1$H-NMR (400 MHz, $CDCl_3$) δ 9.06 (s, 1H), 9.02 (s, 1H), 7.85-7.83 (m, 1H), 7.33 (d, J=8.0 Hz, 2H), 7.04 (d, J=8.0 Hz, 1H), 6.92 (d, J=8.0 Hz, 2H), 4.81 (s, 2H), 4.63 (s, 2H), 3.90

(s, 3H), 2.60 (t, J=4.0 Hz, 2H), 1.71 (s, 2H), 1.34 (s, 6H), 0.71 (s, 9H); $^{13}$C-NMR (100 MHz, $CDCl_3$) δ 166.6, 166.4, 154.8, 149.8, 144.1, 127.4, 127.0, 126.5, 124.1, 121.4, 114.1, 111.1, 67.8, 57.0, 56.8, 52.1, 38.1, 32.3, 31.9, 31.8, 31.6; HRMS [M+H] calcd [$C_{27}H_{34}NO_5$]: 452.2437, Found: 452.2437; Purity: 100% (as determined by RP-HPLC, method A, tR=27.33 min).

Compound 3-28: Methyl 4-(4-methoxybenzyloxy)-3-(2-(4-(2,4,4-trimethylpentan-2-yl)phenoxy)acetamido)benzoate Methyl 4-hydroxy-3-(2-(4-(2,4,4-trimethylpentan-2-yl)phenoxy)acetamido)benzoate (1.0 equiv), anhydrous potassium carbonate (3.0 equiv) and p-methoxy benzyl chloride (2.0 equiv) were mixed in DMF, the resulting mixture was stirred overnight at room temperature and concentrated under reduced pressure, and the obtained residue was diluted with EtOAc and washed with sodium bicarbonate, water and brine. An organic layer was collected and dehydrated with anhydrous $MgSO_4$, and concentrated under reduced pressure. The concentrate was purified by silica gel column chromatography, thereby obtaining methyl 4-(4-methoxybenzyloxy)-3-(2-(4-(2,4,4-trimethylpentan-2-yl)phenoxy)acetamido)benzoate (white solid, 0.11 g, 85.2% yield).

$^1$H-NMR (400 MHz, $CDCl_3$) δ 9.20 (s, 1H), 9.09 (s, 1H), 7.86-7.83 (m, 1H), 7.39 (d, J=8.0 Hz, 2H), 7.21 (d, J=8.0 Hz, 2H), 7.03 (d, J=8.0 Hz, 2H), 6.96 (d, J=8.0 Hz, 2H), 6.53 (d, J=8.0 Hz, 2H), 5.08 (s, 2H), 4.54 (s, 2H), 3.90 (s, 3H), 3.87 (s, 3H), 1.71 (s, 2H), 1.34 (s, 6H), 0.71 (s, 9H); $^{13}$C-NMR (100 MHz, $CDCl_3$) δ 166.8, 166.2, 160.0, 154.6, 151.0, 143.9, 129.9, 129.8, 127.6, 127.2, 126.9, 126.6, 123.3, 120.6, 114.3, 113.9, 110.6, 70.9, 67.5, 57.0, 55.3, 52.0, 38.0, 32.3, 31.8, 31.6; HRMS [M+H] calcd [$C_{32}H_{40}NO_6$]: 534.2856, Found: 534.2856; Purity: 100% (as determined by RP-HPLC, method A, tR=30.37 min).

Compound 3-29: Methyl 3-(2-(4-adamantan-1-yl-phenoxy)-2-methylpropanamido)benzoate 2-(4-adamantan-1-yl-phenoxy)-2-methylpropanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-(4-adamantan-1-yl-phenoxy)-2-methylpropanamido)benzoate (white solid, 0.12 g, 84.5% yield).

$^1$H-NMR (400 MHz, $CDCl_3$) δ 8.74 (s, 1H) 8.14 (t, J=2.0 Hz, 1H), 7.95-7.92 (m, 1H), 7.82-7.79 (m, 1H), 7.43 (t, J=8.0 Hz, 1H), 7.27 (d, J=9.2 Hz, 2H), 6.93 (d, J=8.4 Hz, 2H), 3.91 (s, 3H), 2.09 (brs, 3H), 1.88-1.86 (m, 6H), 1.76-1.74 (m, 6H), 1.57 (s, 6H); $^{13}$C-NMR (100 MHz, $CDCl_3$) δ 173.5, 166.7, 151.3, 147.2, 137.8, 131.0, 129.2, 125.8, 125.4, 124.1, 121.5, 120.6, 81.8, 52.2, 43.3, 36.7, 35.8, 28.9, 25.0; HRMS (EI) m/z [M+H] calcd [$C_{28}H_{34}NO$]: 4448.2488, Found: 448.2488; Purity: 100% (as determined by RP-HPLC, method A, tR=29.60 min).

Compound 3-30: Methyl 3-(2-methyl-2-(4-(2,4,4-trimethylpentan-2-yl)phenoxy)propanamido)benzoate 2-methyl-2-(4-(2,4,4-trimethylpentan-2-yl)phenoxy)propanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(2-methyl-2-(4-(2,4,4-trimethylpentan-2-yl)phenoxy)propanamido)benzoate (white solid, 0.11 g, 75.8% yield).

$^1$H-NMR (400 MHz, $CDCl_3$) δ 8.79 (s, 1H), 8.14 (t, J=2.0 Hz, 1H), 7.96-7.93 (m, 1H), 7.82-7.80 (m, 1H), 7.43 (t, J=8.0 Hz, 1H), 7.28 (d, J=8.4 Hz, 2H), 6.90 (d, J=9.2 Hz, 2H), 3.91 (s, 3H), 1.71 (s, 2H), 1.55 (s, 6H), 1.35 (s, 6H), 0.70 (s, 9H); $^{13}$C-NMR (100 MHz, $CDCl_3$) δ 173.4, 166.6, 151.1, 145.8, 137.8, 130.9, 129.1, 127.1, 125.4, 124.1, 121.4, 120.7, 81.8, 57.1, 52.1, 38.1, 32.3, 31.7, 31.6, 24.9; HRMS (EI) m/z [M+H] calcd [$C_{26}H_{36}NO_4$]: 426.2644, Found: 426.2644; Purity: 100% (as determined by RP-HPLC, method A, tR=28.88 min).

Compound 3-31: Methyl 4-hydroxy-3-(2-methyl-2-(4-(2,4,4-trimethylpentan-2-yl)phenoxy)propanamido)benzoate 2-methyl-2-(4-(2,4,4-trimethylpentan-2-yl)phenoxy)propanoic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 4-hydroxy-3-(2-methyl-2-(4-(2,4,4-trimethylpentan-2-yl)phenoxy)propanamido)benzoate (white solid, 0.03 g, 83.2% yield).

$^1$H-NMR (400 MHz, $CDCl_3$) δ 10.1 (s, 1H), 9.09 (s, 1H), 7.82 (dd, J=8.6 Hz, 1H), 7.77 (d, J=2.0 Hz, 1H), 7.32 (d, J=8.6 Hz, 2H), 7.05 (d, J=8.6 Hz, 1H), 6.93 (d, J=8.6 Hz, 2H), 3.87 (s, 3H), 1.72 (s, 2H), 1.57 (s, 6H), 1.37 (s, 6H), 0.71 (s, 9H); $^{13}$C-NMR (100 MHz, $CDCl_3$) δ 175.7, 166.3, 153.2, 150.5, 146.5, 128.9, 127.2, 124.9, 124.2, 122.2, 122.0, 119.7, 81.7, 57.1, 52.0, 38.2, 32.3, 31.7, 31.5, 24.9; HRMS [M+H] calcd [$C_{26}H_{36}NO_5$]: 442.2515, Found: 442.2576; Purity: 100% (as determined by RP-HPLC, method A, tR=16.29 min).

Compound 3-32: Methyl 3-[4-(4-adamantan-1-yl-phenoxy)butanamido]benzoate 4-(4-(adamantan-1-yl)phenoxy)butanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-[4-(4-adamantan-1-yl-phenoxy)butanamido]benzoate (white solid, 0.11 g, 77.5% yield).

$^{1}$H-NMR (400 MHz, $CDCl_3$) δ 8.35 (s, 1H), 7.83 (d, J=7.6 Hz, 1H), 7.78 (d, J=7.6 Hz, 1H), 7.4 (d, J=8.0 Hz, 2H), 7.28 (s, 1H), 6.86 (d, J=8.8 Hz, 2H), 4.06 (t, J=6.0 Hz, 2H), 3.90 (s, 3H), 2.60 (t, J=7.2 Hz, 2H), 2.18-2.24 (m, 2H), 2.08 (brs, 3H), 1.88-1.86 (m, 6H), 1.76-1.74 (m, 6H); $^{13}$C-NMR (100 MHz, $CDCl_3$) δ 170.9, 166.7, 156.4, 144.1, 138.1, 130.9, 129.2, 125.8, 125.3, 124.2, 120.6, 114.0, 66.8, 52.2, 43.4, 36.8, 35.6, 34.2, 30.9, 29.0, 25.1; HRMS (EI) m/z [M+H] calcd [$C_{28}H_{33}NO_4$]: 448.2488, Found: 448.2478; Purity: 100% (as determined by RP-HPLC, method A, tR=27.50 min).

Compound 3-33: Methyl 3-(4-(4-(2,4,4-trimethylpentan-2-yl)phenoxy)butanamido)benzoate 4-(4-(2,4,4-trimethylpentan-2-yl)phenoxy)butanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 3-(4-(4-(2,4,4-trimethylpentan-2-yl)phenoxy)butanamido)benzoate (white solid, 0.12 g, 82.7% yield).

$^{1}$H-NMR (400 MHz, $CDCl_3$) δ 8.05 (s, 1H), 7.83 (d, J=8.4 Hz, 1H), 7.77 (d, J=7.6 Hz, 1H), 7.49 (s, 1H), 7.38 (t, J=8.0 Hz, 1H), 7.26 (d, J=8.4 Hz, 2H), 6.82 (d, J=8.8 Hz, 2H), 4.04 (t, J=6.6 Hz, 4H), 3.91 (s, 3H), 2.61 (t, J=7.2 Hz, 2H), 2.26-2.19 (m, 2H), 1.70 (s, 2H), 1.34 (s, 6H), 0.71 (s, 9H); $^{13}$C-NMR (100 MHz, $CDCl_3$) δ 171.5, 166.9, 156.3, 142.4, 138.4, 130.6, 129.0, 127.0, 125.1, 124.5, 120.8, 113.6, 66.8, 56.9, 52.2, 37.9, 34.0, 32.7, 31.7, 31.6, 25.1; HRMS (EI) m/z [M+H] calcd [$C_{26}H_{36}NO_4$]: 426.2644, Found: 426.2644; Purity: 100% (as determined by RP-HPLC, method A, tR=26.93 min).

Compound 3-34: Methyl 4-hydroxy-3-(4-(4-(2,4,4-trimethylpentan-2-yl)phenoxy)butanamido)benzoate 4-(4-(2,4,4-trimethylpentan-2-yl)phenoxy)butanoic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 4-hydroxy-3-(4-(4-(2,4,4-trimethylpentan-2-yl)phenoxy)butanamido)benzoate (white solid, 0.10 g, 66.2% yield).

$^{1}$H-NMR (400 MHz, $CDCl_3$) δ 8.10 (s, 1H), 7.80 (dd, J=2.0, 6.4 Hz, 1H), 7.72 (d, J=1.6 Hz, 1H), 7.26 (d, J=8.4 Hz, 2H), 7.01 (d, J=8.4 Hz, 1H), 6.80 (d, J=8.8 Hz, 2H), 4.06 (t, J=5.6 Hz, 2H), 3.86 (s, 3H), 2.72 (t, J=7.2 Hz, 6.8 Hz, 2H), 2.24-2.21 (m, 2H), 1.69 (s, 2H), 1.33 (s, 6H), 0.70 (s, 9H); $^{13}$C-NMR (100 MHz, $CDCl_3$) δ 173.8, 166.8, 156.1, 153.4, 142.8, 128.7, 127.1, 125.8, 124.3, 121.9, 119.6, 113.6 66.7, 56.9, 52.2, 38.0, 33.6, 32.3, 31.8, 31.6, 25.2; HRMS (EI) m/z [M+H] calcd [$C_{26}H_{36}NO_5$]: 442.2593, Found: 442.2593; Purity: 100% (as determined by RP-HPLC, method A, tR=25.63 min).

1-2. Synthesis of Compounds 6-1 to 6-9

As described in FIG. 1, the following Compounds 6-1 to 6-9 were synthesized via Compounds 4 and 5 as intermediates, using Compound 1 as a starting material.

First, processes of synthesizing Compounds 4 and 5 are as follows.

Process of Synthesizing Compound 4:

A mixture of Compound 1 (1.0 equiv) and methyl propiolate (2.0 equiv) in toluene were added to $Ph_3P$ (1.0 equiv) at −10° C. The mixture was heated up to 115° C., and stirred for 2 hours. The solvent was removed under reduced pressure, and the residue was purified by silica gel column chromatography.

Process of Synthesizing Compound 5:

A suspension of an ester compound (Compound 4; 1.0 equiv) in THF/$H_2O$ (1:1) was added to lithium hydroxide monohydrate (3.0 equiv), and stirred overnight at room temperature. The reaction mixture was neutralized with 10% HCl, diluted with EtOA, and successively washed with water-soluble sodium bicarbonate, brine and water. An organic layer was collected, and dehydrated with anhydrous $MgSO_4$. The solvent was filtered, evaporated under reduced pressure, and purified by silica gel column chromatography, thereby obtaining a crude dry product.

Compound 6-1: (E)-3-[3-(4-adamantan-1-yl-phenoxy)-acryloylamino]-benzoic acid methyl ester (E)-3-(4-(adamantan-1-yl)phenoxy)acrylic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-3-[3-(4-adamantan-1-yl-phenoxy)-acryloylamino]-benzoic acid methyl ester (white solid, 0.23 g, 88.5% yield).

$^{1}$H-NMR ($CDCl_3$, 300 MHz) δ 8.06 (s, 1H), 7.89-7.95 (m, 2H), 7.77 (d, J=7.5 Hz, 1H), 7.33-7.42 (m, 3H), 7.02 (d, J=8.7 Hz, 2H), 5.68 (d, J=11.7 Hz, 1H), 3.90 (s, 3H), 2.11 (m, 3H), 1.90 (m, 6H), 1.77 (m, 6H); HRMS (EI) m/z calcd for $C_{27}H_{29}NO_4$ [M+H]: 431.2097, Found: 431.2101.

Compound 6-2: (E)-3-3-[4-(2,4,4-trimethylpentan-2-yl)phenoxy]acrylamidobenzoic acid methyl ester (E)-3-(4-(2,4,4-trimethylpentan-2-yl)phenoxy)acrylic acid (1.0 equiv), methyl 3-aminobenzoate (1.0 equiv) was mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected, dehydrated with anhydrous $MgSO_4$, and concentrated under reduced pressure. The concentrate was purified by silica gel column chromatography, thereby obtaining (E)-3-3-[4-(2,4, 4-trimethylpentan-2-yl)phenoxy]acrylamidobenzoic acid methyl ester (white solid, 0.07 g, 62.8% yield).

$^1$H-NMR (DMSO, 300 MHz) δ 8.05 (m, 1H), 7.89-7.93 (m, 2H), 7.78 (d, J=7.8 Hz, 1H), 7.41 (d, J=8.4 Hz, 1H), 7.37 (d, J=8.4 Hz, 2H), 7.11 (s, 1H), 7.00 (d, J=8.7 Hz, 2H), 5.66 (d, J=11.4 Hz, 1H), 3.91 (s, 3H), 1.73 (s, 2H), 1.37 (s, 6H), 0.72 (s, 9H); HRMS (EI) m/z calcd for $C_{25}H_{31}NO_4$ [$M^+$]: 409.2253, Found: 409.2256.

Compound 6-3: (E)-methyl 4-methyl-3-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and methyl 3-amino-4-methylbenzoate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-methyl 4-methyl-3-(3-(4-(2,4,4-trimethylpentan-2-yl)phenoxy)acrylamido)benzoate (white solid, 0.04 g, 40.2% yield).

$^1$H-NMR (400 MHz, $CDCl_3$) δ 7.93 (d, J=11.6 Hz, 1H), 7.79 (d, J=8.4 Hz, 1H), 7.37 (d, J=8.4 Hz, 2H), 7.29 (s, 1H), 7.01 (d, J=8.8 Hz, 2H), 6.80 (s, 1H), 5.69 (d, J=10.8, 1H), 3.90 (s, 3H), 2.33 (s, 3H), 1.72 (s, 2H), 1.36 (s, 6H), 0.70 (s, 9H); Purity: 99.99% (as determined by RP-HPLC, method A, tR=26.11 min).

Compound 6-4. (E)-methyl 2-methyl-5-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and methyl 5-amino-2-methylbenzoate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-methyl 2-methyl-5-(3-(4-(2,4,4-trimethylpentan-2-yl)phenoxy)acrylamido)benzoate (white solid, 0.04 g, 40.2% yield).

$^1$H-NMR (400 MHz, $CDCl_3$): δ 8.03 (s, 1H), 7.89 (d, J=11.6 Hz, 1H), 7.70 (d, J=6.4 Hz, 1H), 7.53 (s, 1H), 7.34 (d, J=8.4 Hz, 2H), 7.18 (d, J=8.4 Hz, 1H), 6.97 (d, J=8.4 Hz, 2H), 5.71 (d, J=12.0 Hz, 1H), 3.84 (s, 3H), 2.54 (s, 3H), 1.71 (s, 2H), 1.35 (s, 6H), 0.70 (s, 9H); Purity: 99.99% (as determined by RP-HPLC, method A, tR=27.35 min).

Compound 6-5: (E)-methyl 2-hydroxy-5-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and methyl 5-amino-2-hydroxybenzoate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-methyl 2-hydroxy-5-(3-(4-(2,4,4-trimethylpentan-2-yl)phenoxy)acrylamido)benzoate (white solid, 0.03 g, 29.9% yield).

$^1$H-NMR (400 MHz, $CDCl_3$) δ 10.63 (s, 1H), 8.13 (s, 1H), 7.88 (d, J=11.6 Hz, 1H), 7.50 (d, J=8.0 Hz, 1H), 7.35-7.33 (m, 3H), 6.97 (d, J=8.4 Hz, 2H), 6.93 (d, J=8.8 Hz, 1H), 5.68 (d, J=12.0 Hz, 1H), 3.90 (s, 3H), 1.71 (s, 2H), 1.35 (s, 6H), 0.70 (s, 9H); Purity: 99.99% (as determined by RP-HPLC, method A, tR=26.40 min).

Compound 6-6: (E)-isopropyl 3-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and isopropyl 3-aminobenzoate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-isopropyl 3-(3-(4-(2,4,4-trimethylpentan-2-yl)phenoxy)acrylamido)benzoate (white solid, 0.05 g, 48.2% yield).

$^1$H-NMR (400 MHz, $CDCl_3$) δ 7.99 (brs, 2H), 7.92 (d, J=11.6 Hz, 1H), 7.78 (d, J=8.0 Hz, 1H), 7.42-7.35 (m, 3H), 7.31 (s, 1H), 7.00 (d, J=9.2 Hz, 2H), 5.70 (d, J=11.6 Hz, 1H), 5.28-5.21 (m, 1H), 1.72 (s, 2H), 1.37-1.35 (m, 12H), 0.70 (s, 9H); Purity: 99.99% (as determined by RP-HPLC, method A, tR=28.62 min).

Compound 6-7: (E)-methyl 2,4-dimethyl-5-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and methyl 5-amino-2,4-dimethylbenzoate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc and washed with water and brine. An organic layer was collected, dehydrated with anhydrous $MgSO_4$, and concentrated under reduced pressure. The concentrate was purified by silica gel column chromatography, thereby obtaining (E)-methyl 2,4-dimethyl-5-(3-(4-(2,4,4-trimethylpentan-2-yl)phenoxy)acrylamido)benzoate (white solid, 0.07 g, 57.3% yield).

$^1$H-NMR (400 MHz, $CDCl_3$) δ 8.33 (s, 1H), 7.91 (d, J=11.6 Hz, 1H), 7.35 (d, J=8.8 Hz, 2H), 7.06 (s, 1H), 6.99 (d, J=8.4, 2H), 6.91 (s, 1H), 5.70 (brs, 1H), 3.85 (s, 3H), 2.54 (s, 3H), 2.25 (s, 3H), 1.72 (s, 2H), 1.35 (s, 6H), 0.70 (s, 9H); Purity: 99.99% (as determined by RP-HPLC, method A, tR=27.02 min).

Compound 6-8: (E)-3H-[1,2,3]triazolo[4,5-b]pyridin-3-yl 3-(4-(2,4,4-trimethylpentan-2-yl)phenoxy)acrylate (E)-3-(4-(2,4,4-trimethylpentan-2-yl)phenoxy)acrylic acid (1.0 equiv) and methyl 5-aminothiophene-2-carboxylate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc and washed with water and brine. An organic layer was collected, dehydrated with anhydrous $MgSO_4$, and concentrated under reduced pressure. The concentrate was purified by silica gel column chromatography, thereby obtaining (E)-3H-[1,2,3]triazolo[4,5-b]pyridin-3-yl 3-(4-(2,4,4-trimethylpentan-2-yl)phenoxy)acrylate (white solid, 0.05 g, 44.6% yield).

$^1$H-NMR (400 MHz, $CDCl_3$) δ 8.74 (d, J=4.4 Hz, 1H), 8.44 (d, J=8.0 Hz, 1H), 8.18 (d, J=12.0 Hz, 1H), 7.46-7.41 (m, 3H), 7.06 (d, J=8.8 Hz, 2H), 5.83 (d, J=12.0 Hz, 1H), 1.75 (s, 2H), 1.37 (s, 6H), 0.71 (s, 9H).

Compound 6-9: (E)-1H-benzo[d][1,2,3]triazol-1-yl 3-(4-(2,4,4-trimethylpentan-2-yl)phenoxy)acrylate (E)-3-(4-(2,4,4-trimethylpentan-2-yl)phenoxy)acrylic acid (1.0 equiv) and methyl 2-aminoisonicotinate (1.0 equiv) were mixed in DMF, and the resulting mixture was added to HATU (1.2 equiv) and DIPEA (0.7 equiv). The reaction mixture was stirred overnight at room temperature and concentrated under reduced pressure, and the obtained residue was diluted with EtOAc, and washed with water and brine. An organic layer was collected, dehydrated with anhydrous $MgSO_4$, and concentrated under reduced pressure. The concentrate was purified by silica gel column chromatography, thereby obtaining (E)-1H-benzo[d][1,2,3]triazol-1-yl 3-(4-(2,4,4-trimethylpentan-2-yl)phenoxy)acrylate (white solid, 0.05 g, 54.0% yield).

$^1$H-NMR (400 MHz, $CDCl_3$) δ 8.25 (d, J=13.6 Hz, 1H), 8.04 (d, J=8.4 Hz, 1H), 7.77 (d, J=4.0 Hz, 2H), 7.56-7.52 (m, 1H), 7.41 (d, J=8.8 Hz, 2H), 7.09 (d, J=8.4 Hz, 2H), 6.71 (d, J=13.6 Hz, 1H), 1.74 (s, 2H), 1.38 (s, 6H), 0.73 (s, 9H).

Compound 6-10: (E)-methyl 4-hydroxy-3-(3-(4-(2,4,4-trimethylpentan-2-yl)phenoxy)acrylamido)benzoate (E)-3-(4-(2,4,4-trimethylpentan-2-yl)phenoxy)acrylic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected, dehydrated with anhydrous $MgSO_4$, and concentrated under reduced pressure. The concentrate was purified by silica gel column chromatography, thereby obtaining (E)-methyl 4-hydroxy-3-(3-(4-(2,4,4-trimethylpentan-2-yl)phenoxy)acrylamido)benzoate (white solid, 0.01 g, 56.2% yield).

$^1$H-NMR (400 MHz, $CDCl_3$) δ 10.47 (s, 1H), 7.97 (d, J=11.2 Hz, 1H), 7.80 (dd, J=2.0, 9.0 Hz, 1H), 7.67 (d, J=2.0 Hz, 1H), 7.39 (d, J=8.8 Hz, 2H), 7.00-7.02 (m, 3H), 5.73 (d, J=11.2 Hz, 1H), 3.88 (s, 3H), 1.74 (s, 2H), 1.37 (s, 6H), 0.72 (s, 9H); $^{13}$C-NMR (100 MHz, $CDCl_3$) δ 167.0, 166.7, 160.2, 153.8, 153.5, 147.3, 128.8, 127.7, 125.9, 124.2, 121.8, 120.0, 117.1, 101.8, 56.9, 52.1, 38.3, 32.3, 31.7, 31.6; HRMS (EI) m/z calcd for $C_{25}H_{32}NO_5$ [M+H]: 426.2202, Found: 426.2286; Purity: 99.99% (as determined by RP-HPLC, method A, tR=26.18 min).

1-3. Synthesis of Compounds 9-1 and 9-11

The following Compounds 9-1 to 9-11 were synthesized using Compound 1 as a starting material and Compound 8 as an intermediate.

First, a process of synthesizing Compound 8 is as follows.

Process of Synthesizing Compound 8:

A methanol solution of methyl acrylic acid ester (Compound 4, 1.0 equiv) was treated with 10% Pd/C (10% w/w). The reaction product was hydrogenated under 1 atm hydrogen atmospheric pressure at room temperature, and stirred overnight. After the completion of the reaction, the mixture was filtered through a Celite® pad and concentrated. The resulting product was purified by silica gel column chromatography. A THF/$H_2O$ (1:1) suspension of methyl ester (Compound 7) was added to lithium hydroxy monohydrate (4.0 equiv), and stirred overnight at room temperature. The reaction mixture was neutralized with 10% HCl, diluted with EtOA, and successively washed with water-soluble sodium bicarbonate, brain and water. An organic layer was collected and dehydrated with anhydrous $MgSO_4$. The solvent was filtered, evaporated under reduced pressure, and purified using silica gel column chromatography, thereby obtaining a crude dry product.

Compound 9-1: Methyl 3-(3-(4-(adamantan-1-yl)phenoxy)propanamido)benzoate 3-(4-adamantan-1-yl-phenoxy)-propanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected, dehydrated with anhydrous $MgSO_4$, and concentrated under reduced pressure. The concentrate was purified by silica gel column chromatography, thereby obtaining methyl 3-(3-(4-(adamantan-1-yl)phenoxy)propanamido)benzoate (white solid, 0.12 g, 83.3% yield).

$^1$H-NMR (400 MHz, $CDCl_3$) δ 8.29 (s, 1H), 7.79-7.82 (m, 2H), 7.54 (d, J=7.6 Hz, 1H), 7.48 (d, J=8.0 Hz, 2H), 6.91 (d, J=8.8 Hz, 2H), 4.32 (t, J=6.0 Hz, 2H), 3.89 (s, 3H), 2.65 (t, J=7.2 Hz, 2H), 2.02 (brs, 3H), 1.99-1.97 (m, 6H), 1.77-1.71 (m, 6H); $^{13}$C-NMR (100 MHz, $CDCl_3$) δ 169.2, 166.7, 155.7, 144.9, 138.0, 130.9, 129.1, 126.1, 125.4, 124.4, 120.8, 114.2, 64.2, 52.2, 43.4, 36.8, 35.6, 29.6, 28.8; HRMS (EI) m/z [M+H] calcd [$C_{27}H_{31}NO_4$]: 433.2253, Found: 433.2257; Purity: 100% (as determined by RP-HPLC, method A, tR=26.80 min).

Compound 9-2: Methyl 3-(3-(4-(2,4,4-trimethylpentan-2-yl)phenoxy)propanamido)benzoate 3-(4-(2,4,4-trimethylpentan-2-yl)phenoxy)propanoic acid (1.0 equiv) and methyl 3-aminobenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was dehydrated with anhydrous $MgSO_4$, and concentrated under reduced pressure. The concentrate was purified by silica gel column chromatography, thereby obtaining methyl 3-(3-(4-(2,4,4-trimethylpentan-2-yl)phenoxy)propanamido)benzoate (white solid, 0.13 g, 88.4% yield).

$^1$H-NMR (400 MHz, $CDCl_3$) δ 8.18 (s, 1H), 8.07 (t, J=1.6 Hz, 1H), 7.88-7.86 (m, 1H), 7.77 (d, J=8.0 Hz, 1H), 7.38 (t, J=8.0 Hz, 1H), 7.29 (d, J=8.8 Hz, 2H), 6.86 (d, J=9.2 Hz, 2H), 4.32 (t, J=4.0 Hz, 2H), 3.89 (s, 3H), 2.85 (t, J=4.0 Hz,

2H), 1.70 (s, 2H), 1.34 (s, 6H), 0.71 (s, 9H); $^{13}$C-NMR (100 MHz, $CDCl_3$) δ 169.2, 166.7, 155.6, 143.4, 138.0, 130.9, 129.2, 127.3, 125.4, 124.4, 120.8, 113.8, 64.1, 56.9, 52.2, 38.0, 37.8, 32.3, 31.8, 31.6, 29.7; HRMS (EI) m/z [M+H] calcd [$C_{25}H_{34}NO_4$]: 412.2488, Found 412.2488; Purity: 100% (as determined by RP-HPLC, method A, tR=26.00 min).

Compound 9-3: Methyl 4-hydroxy-3-(3-(4-(2,4,4-trimethylpentan-2-yl)phenoxy)propanamido)benzoate 3-(4-(2,4,4-trimethylpentan-2-yl)phenoxy)propanoic acid (1.0 equiv) and methyl 3-amino-4-hydroxybenzoate (1.0 equiv) were mixed in DMF, and the resulting mixture was added to EDC·HCl (1.2 equiv), HOBT (1.2 equiv) and DIPEA (2.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 4-hydroxy-3-(3-(4-(2,4,4-trimethylpentan-2-yl)phenoxy)propanamido)benzoate (white solid, 0.01 g, 75.0% yield).

$^1$H-NMR (400 MHz, $CDCl_3$) δ 9.74 (s, 1H), 8.36 (s, 1H), 7.81 (dd, J=2.0 Hz, 1H), 7.67 (d, J=2.0 Hz, 1H), 7.32 (d, J=8.8 Hz, 1H), 7.03 (d, J=8.4 Hz, 1H), 6.89 (d, J=8.4 Hz, 2H), 4.35 (t, J=5.4 Hz, 2H), 3.88 (s, 3H), 2.94 (t, J=5.6 Hz, 2H), 1.71 (s, 2H), 1.34 (s, 6H), 0.71 (s, 9H); $^{13}$CNMR (100 MHz, $CDCl_3$) δ 171.7, 166.4, 155.3, 153.2, 143.7, 128.9, 127.3, 125.5, 124.2, 122.1, 119.7, 113.9, 63.8, 56.9, 52.1, 38.0, 36.8, 32.3, 31.7, 31.6; HRMS (EI) m/z calcd for $C_{25}H_{34}NO_5$ [M+H]: 428.2359, Found: 428.2431; Purity: 99.99% (as determined by RP-HPLC, method A, tR=24.09 min).

Compound 9-4: Methyl 4-methyl-3-(3-(4-(2,4,4-trimethylpentan-2-yl)phenoxy)propanamido)benzoate 3-(4-(2,4,4-trimethylpentan-2-yl)phenoxy)propanoic acid (1.0 equiv) and methyl 3-amino-4-methylbenzoate (1.2 equiv) were mixed in THF, and the resulting mixture was added to HATU (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 4-methyl-3-(3-(4-(2,4,4-trimethylpentan-2-yl)phenoxy)propanamido)benzoate (white solid, 0.02 g, 28.2% yield).

$^1$H-NMR (500 MHz, $CDCl_3$) δ 8.55 (s, 1H), 7.98 (s, 1H), 7.75-7.77 (m, 1H), 7.31 (d, J=9.0 Hz, 2H), 7.24 (d, J=8.5 Hz, 1H), 6.88 (d, J=9.0 Hz, 2H), 4.35 (t, J=5.5 Hz, 2H), 3.90 (s, 3H), 2.92 (t, J=5.5 Hz, 2H), 2.28 (s, 3H), 1.72 (s, 2H), 1.36 (s, 6H), 0.72 (s, 9H); $^{13}$C-NMR (125 MHz, $CDCl_3$) δ 169.4, 166.8, 155.5, 143.4, 135.9, 134.3, 130.5, 128.8, 127.4, 126.2, 123.9, 113.6, 64.1, 57.0, 52.1, 38.0, 37.7, 32.3, 31.8, 31.7, 18.2.

Compound 9-5: Methyl 2-methyl-5-(3-(4-(2,4,4-trimethylpentan-2-yl)phenoxy)propanamido)benzoate 3-(4-(2,4,4-trimethylpentan-2-yl)phenoxy)propanoic acid (1.0 equiv) and methyl 5-amino-2-methylbenzoate (1.2 equiv) were mixed in DMF, and the resulting mixture was added to HATU (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 2-methyl-5-(3-(4-(2,4,4-trimethylpentan-2-yl)phenoxy)propanamido)benzoate (yellow solid, 0.05 g, 61.0% yield).

$^1$H-NMR (500 MHz, $CDCl_3$) δ 8.06 (s, 1H), 8.01 (d, J=2.0 Hz, 1H), 7.65-7.67 (m, 1H), 7.30 (d, J=8.5 Hz, 2H), 7.19 (d, J=8.5 Hz, 1H), 6.87 (d, J=9.0 Hz, 2H), 4.32 (t, J=6.0 Hz, 2H), 3.87 (s, 3H), 2.84 (t, J=5.0 Hz, 2H), 2.55 (s, 3H), 1.72 (s, 2H), 1.35 (s, 6H), 0.72 (s, 9H); $^{13}$C-NMR (125 MHz, $CDCl_3$) δ 169.2, 167.6, 155.7, 143.3, 136.1, 135.6, 132.3, 129.8, 127.3, 123.7, 121.9, 113.8, 64.1, 56.9, 52.0, 38.0, 37.7, 32.3, 31.8, 31.7, 21.2.

Compound 9-6: Methyl 2-hydroxy-5-(3-(4-(2,4,4-trimethylpentan-2-yl)phenoxy)propanamido)benzoate A solution of 1,1-carbonyldiimidazole (CDI) (1.0 equiv) in THF was partially added, and stirred for 45 minutes at room temperature. In a different flask, imidazole (1.1 equiv) was added to a solution of methyl 5-amino-2-hydroxybenzoate (0.9 equiv) in THF. The acid/CDI mixture was added to an aniline-imidazole solution, and stirred overnight under argon. The solvent was evaporated under vacuum, and the resulting product was purified by silica gel column chromatography (white solid, 0.08 g, 33.4% yield).

$^1$H-NMR (500 MHz, $CDCl_3$) δ 10.64 (s, 1H), 8.10 (d, J=3.0 Hz, 1H), 7.89 (brs, 1H), 7.47 (dd, J=3.0, 8.5 Hz, 1H), 7.31 (d, J=9.0 Hz, 2H), 6.94 (d, J=9.0 Hz, 1H), 6.87 (d, J=9.0 Hz, 2H), 4.33 (t, J=6.0 Hz, 2H), 3.93 (s, 3H), 2.83 (t, J=6.0 Hz, 2H), 1.72 (s, 2H), 1.35 (s, 6H), 0.72 (s, 9H); $^{13}$C-NMR (125 MHz, $CDCl_3$) δ 170.2, 169.1, 158.5, 155.6, 143.3, 129.4, 128.7, 127.3, 121.6, 117.9, 113.8, 112.1, 64.1, 56.9, 52.4, 38.0, 37.5, 32.3, 31.8, 31.7.

Compound 9-7: Isopropyl 3-(3-(4-(2,4,4-trimethylpentan-2-yl)phenoxy)propanamido)benzoate 3-(4-(2,4,4-trimethylpentan-2-yl)phenoxy)propanoic acid (1.0 equiv) and isopropyl 3-aminobenzoate (1.2 equiv) were mixed in DMF, and the resulting mixture was added to HATU (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining isopropyl 3-(3-(4-(2,4,4-trimethylpentan-2-yl)phenoxy)propanamido)benzoate (transparent liquid, 0.06 g, 26.5% yield).

$^1$H-NMR (500 MHz, $CDCl_3$) 7.99 (brs, 2H), 7.93 (d, J=7.0 Hz, 1H), 7.79 (d, J=7.0 Hz, 1H), 7.41 (t, J=8.0 Hz, 1H), 7.32 (d, J=9.0 Hz, 2H), 6.89 (d, J=8.0 Hz, 2H), 5.25 (m, 1H), 4.35 (t, J=6.0 Hz, 2H), 2.87 (t, J=6.0 Hz, 2H), 1.72 (s, 2H), 1.38 (d, J=6.5 Hz, 6H), 1.36 (s, 6H), 0.72 (s, 9H); $^{13}$C-NMR (125 MHz, $CDCl_3$) δ 169.2, 165.7, 155.6, 143.4, 137.9, 131.6, 129.1, 127.3, 125.3, 124.3, 120.6, 113.8, 68.6, 64.1, 56.9, 38.0, 37.8, 32.3, 31.8, 31.7, 21.9.

Compound 9-8: Methyl 5-(3-(4-(2,4,4-trimethylpentan-2-yl)phenoxy)propanamido)nicotinate 3-(4-(2,4,4-trimethylpentan-2-yl)phenoxy)propanoic acid (1.0 equiv) and methyl 5-aminonicotinate (1.2 equiv) were mixed in THF, and the resulting mixture was added to EDC·HCl (1.5 equiv), HOBT (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining methyl 5-(3-(4-(2,4,4-trimethylpentan-2-yl)phenoxy)propanamido)nicotinate (white solid, 0.06 g, 40.3% yield).

$^1$H-NMR (500 MHz, $CDCl_3$) δ 8.97 (d, J=1.5 Hz, 1H), 8.84 (d, J=2.5 Hz, 1H), 8.64 (t, J=2.0 Hz, 1H), 8.27 (s, 1H), 7.32 (d, J=9.0 Hz, 2H), 6.88 (d, J=8.5 Hz, 2H), 4.35 (t, J=5.0 Hz, 2H), 3.95 (s, 3H), 2.91 (t, J=5.5 Hz, 2H), 2.72 (s, 2H), 1.35 (s, 6H), 0.72 (s, 9H); $^{13}$C-NMR (125 MHz, $CDCl_3$) δ 169.7, 165.5, 155.4, 146.3, 144.8, 143.7, 127.7, 127.4, 113.8, 63.9, 56.9, 52.6, 38.0, 37.6, 32.3, 31.8, 31.7.

Compound 9-9: N-(3-(morpholine-4-carbonyl)phenyl)-3-(4-(2,4,4-trimethylpentan-2-yl)phenoxy)propanamide 3-(4-(2,4,4-trimethylpentan-2-yl)phenoxy)propanoic acid (1.0 equiv) and (3-aminophenyl)(morpholino)methanone (1.2 equiv) were mixed in THF, and the resulting mixture was added to EDC·HCl (1.5 equiv), HOBT (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining N-(3-(morpholine-4-carbonyl)phenyl)-3-(4-(2,4,4-trimethylpentan-2-yl)phenoxy)propanamide (white solid, 0.08 g, 53.0% yield).

$^1$H-NMR (500 MHz, $CDCl_3$) δ 8.56 (s, 1H), 7.57-7.60 (m, 2H), 7.27-7.33 (m, 3H), 7.10 (d, J=8.0 Hz, 1H), 6.85 (d, J=8.5 Hz, 2H), 4.30 (t, J=5.5 Hz, 2H), 3.46-3.77 (m, 8H), 2.81 (t, J=5.5 Hz, 2H), 1.71 (s, 2H), 1.35 (s, 6H), 0.72 (s, 9H); $^{13}$C-NMR (125 MHz, $CDCl_3$) δ 170.1, 169.3, 155.7, 143.2, 138.3, 135.7, 129.3, 127.3, 122.5, 121.4, 118.7, 113.7, 66.9, 64.0, 56.9, 38.0, 37.6, 32.3, 31.8, 31.7, 22.7, 14.2.

Compound 9-10: Ethyl 2-(3-(3-(4-(2,4,4-trimethylpentan-2-yl)phenoxy)propanamido)benzamido)acetate 3-(4-(2,4,4-trimethylpentan-2-yl)phenoxy)propanoic acid (1.0 equiv) and ethyl 2-(3-aminobenzamido)acetate (1.2 equiv) were mixed in THF, and the resulting mixture was added to EDC·HCl (1.5 equiv), HOBT (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining ethyl 2-(3-(3-(4-(2,4,4-trimethylpentan-2-yl)phenoxy)propanamido)benzamido)acetate (white solid, 0.14 g, 64.4% yield).

$^1$H-NMR (500 MHz, $CDCl_3$) δ 8.47 (s, 1H), 7.86 (s, 1H), 7.83 (d, J=8.0 Hz, 1H), 7.49 (d, J=8.0 Hz, 1H), 7.28-7.34 (m, 3H), 6.99 (s, 1H), 6.86 (d, J=8.5 Hz, 2H), 4.32 (t, J=5.5 Hz, 2H), 4.20-4.26 (m, 4H), 2.85 (d, J=5.0 Hz, 2H), 1.70 (s, 2H), 1.34 (s, 6H), 1.30 (t, J=7.0 Hz, 3H), 0.71 (s, 9H); $^{13}$C-NMR (125 MHz, $CDCl_3$) δ 170.2, 169.4, 167.4, 155.7, 143.2, 138.4, 134.2, 129.3, 127.3, 123.2, 122.6, 118.4, 113.8, 64.0, 61.7, 56.9, 41.9, 38.0, 37.6, 32.3, 31.8, 31.7, 14.2.

Compound 9-11: (S)-methyl 3-methyl-2-(3-(3-(4-(2,4,4-trimethylpentan-2-yl)phenoxy)propanamido)benzamido)butanoate 3-(4-(2,4,4-trimethylpentan-2-yl)phenoxy)propanoic acid (1.0 equiv) and (S)-methyl 2-(3-aminobenzamido)-3-methylbutanoate (1.2 equiv) were mixed in THF, and the resulting mixture was added to EDC·HCl (1.5 equiv), HOBT (1.5 equiv) and DIPEA (1.5 equiv). The reaction mixture was stirred overnight at room temperature and concentrated under reduced pressure, and the obtained residue was diluted with EtOAc and washed with water and brine. An organic layer was collected and dehydrated with anhydrous $MgSO_4$, and concentrated under reduced pressure. The concentrate was purified by silica gel column chromatography, thereby obtaining (S)-methyl 3-methyl-2-(3-(3-(4-(2,4,4-trimethylpentan-2-yl)phenoxy)propanamido)benzamido)butanoate (white solid, 0.15 g, 73.3% yield).

$^1$H-NMR (500 MHz, $CDCl_3$) δ 8.60 (s, 1H), 7.90 (s, 1H), 7.89 (s, 1H), 7.47 (d, J=7.5 Hz, 1H), 7.34 (t, J=8.0 Hz, 1H), 7.27 (d, J=9.0 Hz, 2H), 6.81-6.86 (m, 3H), 4.72-4.75 (m, 1H), 4.31 (t, J=5.5 Hz, 2H), 3.75 (s, 3H), 2.85 (t, J=5.5 Hz, 2H), 2.33-2.30 (m, 1H), 1.70 (s, 2H), 1.34 (s, 6H), 0.99 (t, J=6.5 Hz, 6H), 0.71 (s, 9H); $^{13}$C-NMR (125 MHz, $CDCl_3$) δ 172.6, 169.4, 167.3, 155.8, 143.0, 138.6, 134.7, 129.3, 127.2, 123.2, 122.4, 118.5, 113.8, 64.0, 57.8, 56.9, 52.3, 38.0, 37.6, 32.3, 31.8, 31.7, 31.4, 19.1, 18.1.

EXPERIMENTAL EXAMPLES

Experimental Example 1. Confirmation of MDH Inhibitory Activity of Prepared Compounds 1-1. MDH2 Gene Cloning and Recombinant Protein Isolation and Purification To verify the MDH2 inhibitory activity of the compound prepared according to Example 1, an MDH2 recombinant protein was prepared. The MDH2 gene was purchased from Korean Human Gene Bank (KUGI, NM_005918), amplified by PCR, and then cloned using a pET28a vector (Merck, Germany). Afterward, the plasmid vector was introduced into *E. coli* Rosetta 2 (DE3), and an MDH2 recombinant protein was overexpressed by IPTG treatment.

Figure 2:
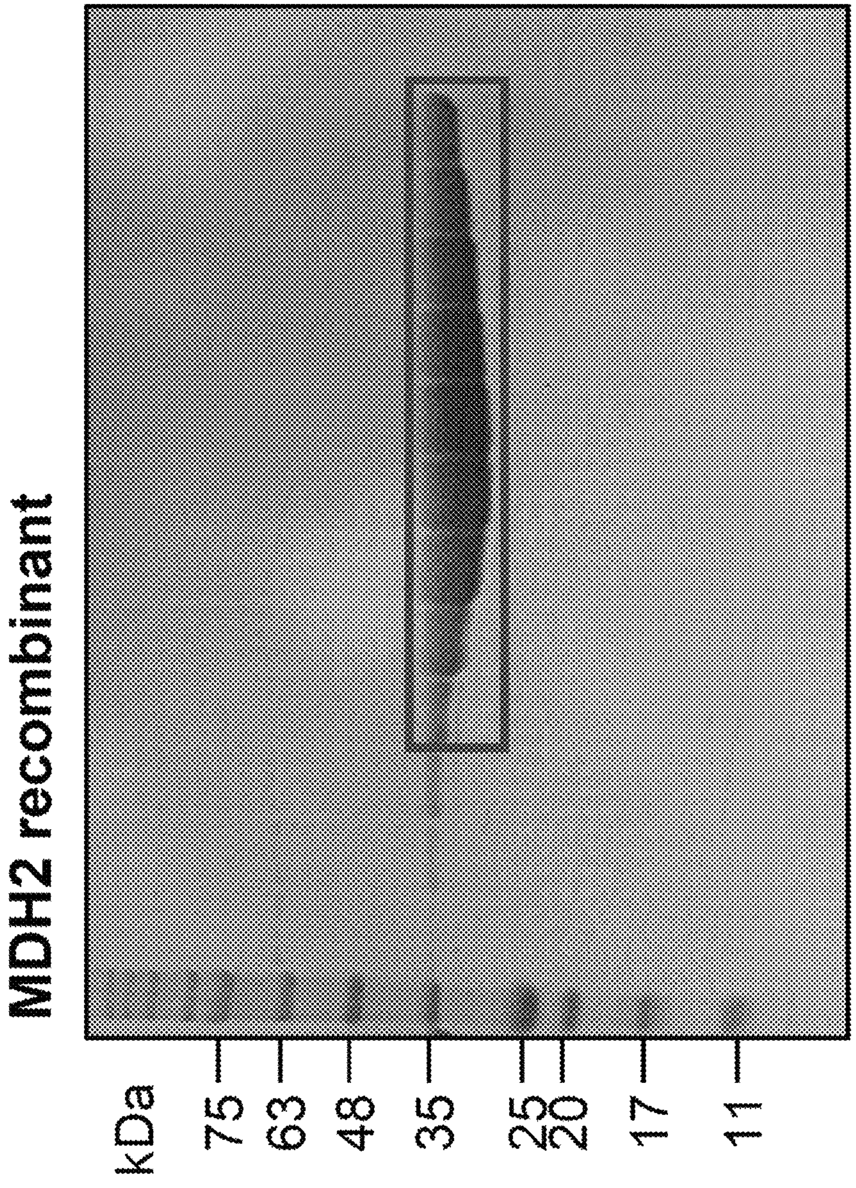
FIG. 2 shows the overexpressed recombinant MDH2 protein, which is isolated and purified in the present invention.

As a result, as shown in FIG. 2, the overexpressed recombinant MDH2 protein was isolated and purified through Ni-NTA affinity chromatography, TEV enzyme cleavage, and size-exclusion chromatography.

1-2. Confirmation of MDH1 and MDH2 Inhibitory Activity of Prepared Compounds (In Vitro)

The inhibitory activity of the prepared compounds against MDH1 recombinant protein and the MDH2 recombinant proteins prepared in each of Experimental Examples 1-1, 1-2, 1-3 and 1-4 was measured. More specifically, 0.25 nM MDH1 recombinant protein (Biovision) or MDH2 recombinant protein was added to 200 μM oxaloacetate, nicotinamide adenine dinucleotide (NADH), the compound prepared in Example 1 and an MDH assay buffer (100 mM potassium phosphate, pH 7.4) to allow a reaction for 30 minutes. Afterward, a change in NADH concentration in the solution due to NADH oxidation ($NAD^+$) by an MDH1 or MDH2 enzyme was analyzed by measuring absorbance at 340 nm.

As a result, as shown in Table 1 below, SAR results for 55 types of the compounds described in Example 1 were confirmed.

TABLE 1

| Comp. No. | MDH1 $IC_{50}$ (μM) | MDH2 $IC_{50}$ (μM) |
|---|---|---|
| 3-1 | + | + |
| 3-2 | + | + |
| 3-3 | + | + |
| 3-4 | + | + |
| 3-5 | + | + |
| 3-6 | + | + |
| 3-7 | ++ | + |
| 3-8 | ++ | + |
| 3-9 | + | + |
| 3-10 | + | + |
| 3-11 | ++ | ++ |
| 3-12 | +++ | +++ |
| 3-13 | +++ | +++ |
| 3-14 | +++ | +++ |
| 3-15 | +++ | ++ |
| 3-16 | + | + |
| 3-17 | +++ | ++ |
| 3-18 | + | + |
| 3-19 | + | + |
| 3-20 | +++ | ++ |
| 3-21 | + | + |
| 3-22 | + | + |
| 3-23 | + | + |
| 3-24 | +++ | + |
| 3-25 | + | + |
| 3-26 | + | + |
| 3-27 | +++ | +++ |
| 3-28 | +++ | +++ |
| 3-29 | +++ | +++ |
| 3-30 | +++ | +++ |
| 3-31 | +++ | + |
| 3-32 | +++ | +++ |
| 3-33 | +++ | +++ |
| 3-34 | ++ | +++ |
| 6-1 | + | +++ |
| 6-2 | +++ | +++ |
| 6-3 | ++ | ++ |
| 6-4 | + | + |
| 6-5 | + | + |
| 6-6 | + | + |
| 6-7 | ++ | + |
| 6-8 | ++ | ++ |
| 6-9 | + | + |
| 6-10 | +++ | +++ |
| 9-1 | +++ | ++ |
| 9-2 | +++ | +++ |
| 9-3 | +++ | +++ |
| 9-4 | ++ | ++ |
| 9-5 | + | + |
| 9-6 | + | + |
| 9-7 | + | + |
| 9-8 | ++ | ++ |
| 9-9 | + | + |
| 9-10 | + | + |
| 9-11 | + | + |

1~5 μM: +++,
5~10 μM: ++,
>10 μM: +

Experimental Example 2. Confirmation of MDH Inhibiting Mechanism of Compound 9-2

The MDH inhibiting mechanism of Compound 9-2 prepared in Example 1-3, that is, methyl 3-(3-(4-(2,4,4-trimethylpentan-2-yl)phenoxy)propanamido)benzoate, was confirmed. More specifically, as described in Experimental Example 1-2, enzyme kinetic experiments were performed using various concentrations (60, 75, 100, 150 and 300 μM) of NADH and 600 μM oxaloacetate. In addition, the maximum velocity (Vmax) and the Michaelis constant (Km) were determined by the Lineweaver-Buck plot method.

Figure 3:
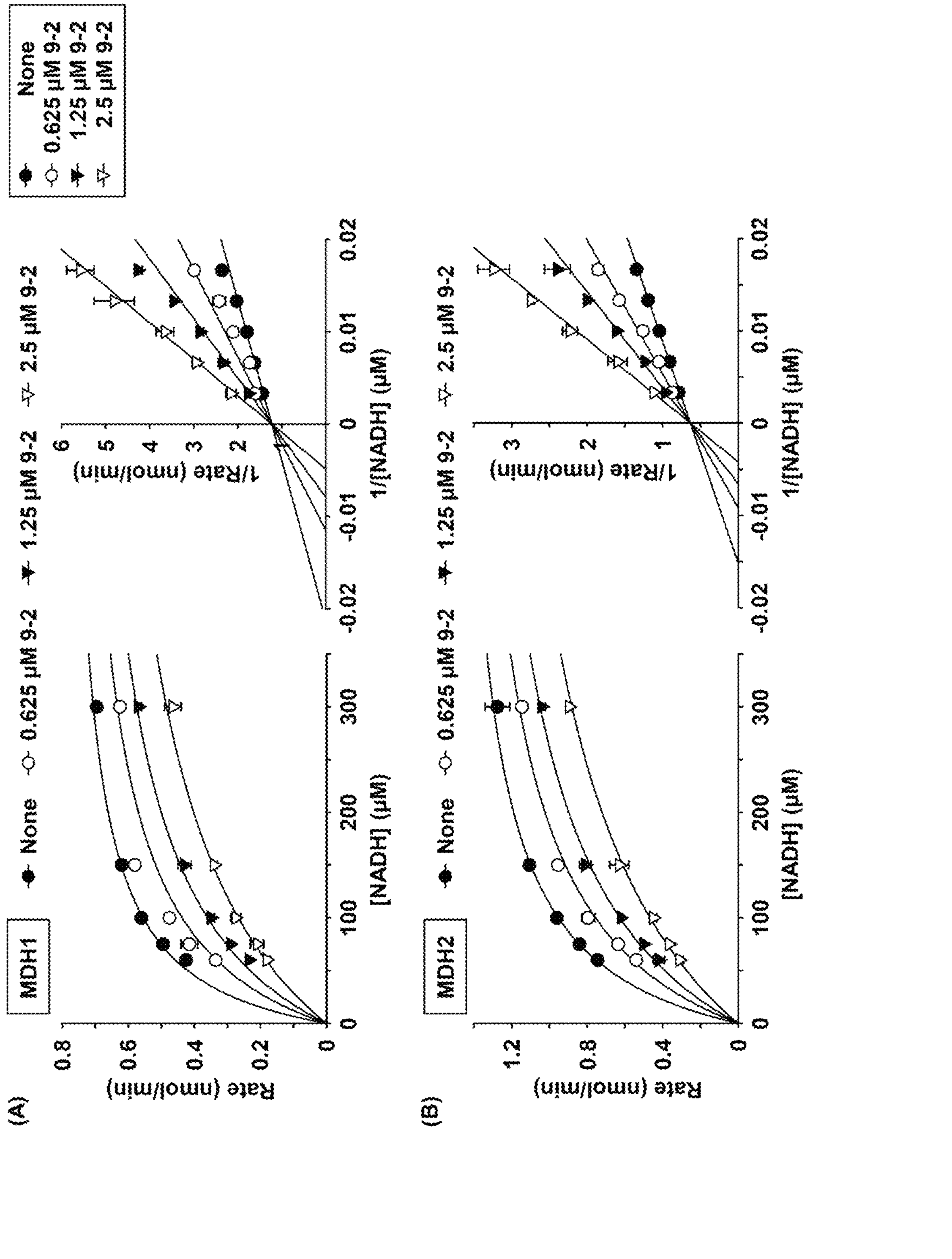
FIG. 3 shows the result of measuring enzyme kinetics of MDH1 and MDH2 according to the change in NADH concentration of a compound of the present invention.

As a result, as shown in FIG. 3, three types of lines obtained from different concentrations of Compound 9-2 in MDH1 and MDH2 enzyme reactions crossed the x axis, and as an NADH concentration changes, the $V_{max}$ value does not change, but the binding affinity (Km) value was reduced in a concentration-dependent manner. Therefore, it was confirmed that Compound 9-2 binds to the same binding site as NADH, thereby competitively inhibiting MDH.

Experimental Example 3. Confirmation of HIF-1α Inhibitory Activity of Compound 9-2

The HIF-1α inhibitory activity of Compound 9-2 prepared in Example 1-3 was confirmed. Hypoxia-inducible factor-1α (HIF-1α) is a factor that affects radioresistance and chemoresistance in solid cancer and malignancy of cancer. More specifically, an HCT-116 colorectal cancer cell line was suspended in DMEM containing 5% fetal bovine serum (FBS), transferred to a 6-well plate ($5\times10^5$ cells/well), and cultured in a 37 D cell incubator maintaining 5% carbon dioxide for 24 hours. To induce the accumulation of HIF-1a protein by hypoxia, the cells were cultured under 1% oxygen, 94% nitrogen and 5% carbon dioxide conditions for 6 hours. The HCT-116 cells were disrupted using a radioimmunoprecipitation assay buffer (RIPA buffer, Millipore), thereby obtaining a cell extract, and 10 μg each of the cell extract was isolated through SDS-PAGE, transferred to a polyvinylidene fluoride (PVDF) membrane, followed by sequentially binding of a HIF-1α antibody (BD Biosciences), a HIF-1β antibody (BD Biosciences), a β-Actin (SantaCruz) and horseradish peroxidase (HRP)-labeled secondary antibody (SantaCruz) to confirm protein expression.

Figure 4:
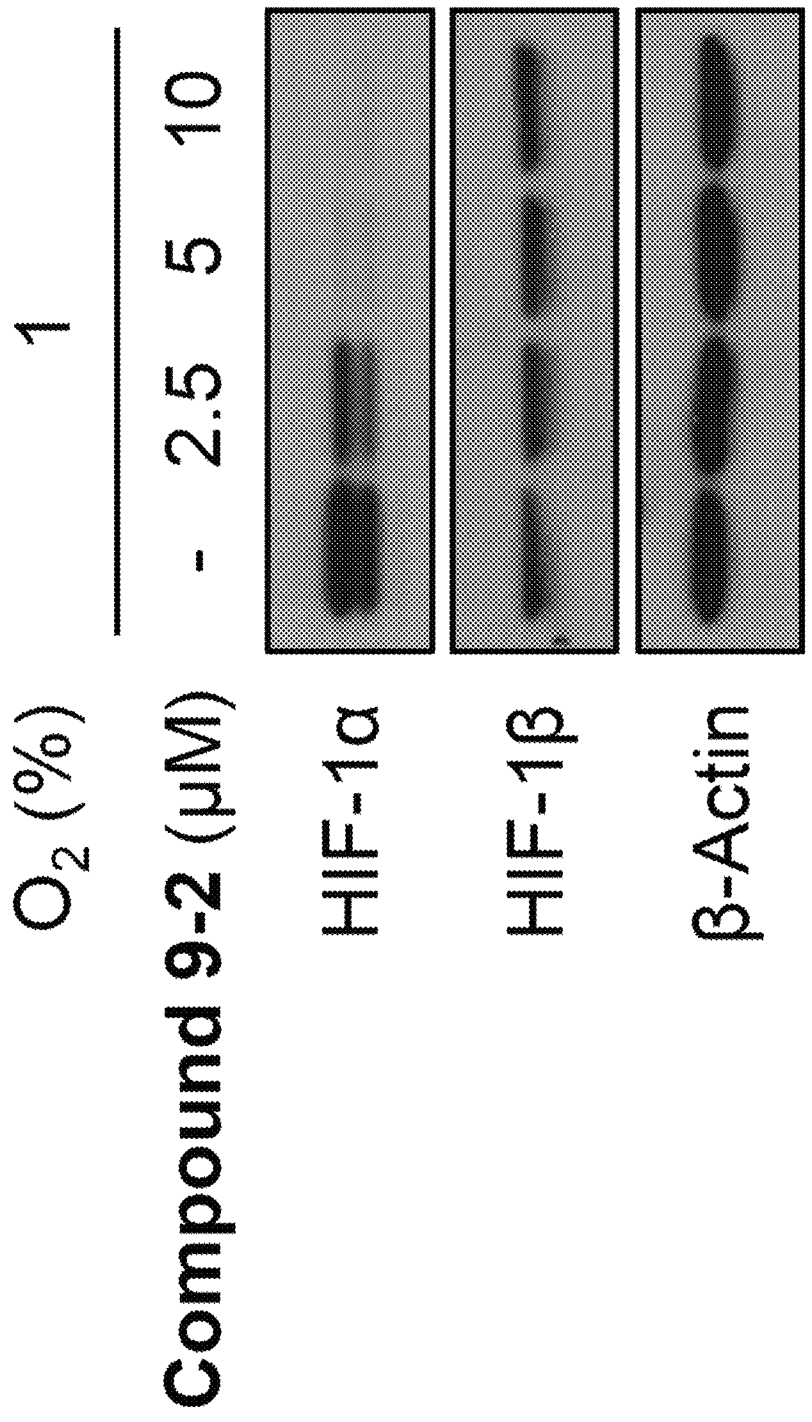
FIG. 4 shows the result of confirming the HIF-1α inhibitory activity of a compound of the present invention using immunoblot analysis.

As a result, as shown in FIG. 4, it was confirmed that Compound 9-2 inhibits HIF-1α protein accumulation in a concentration-dependent manner without affecting HIF-1β protein expression at 2.5, 5 and 10 μM.

Experimental Example 4. Confirmation of Inhibition of Mitochondrial Respiration of Compound 9-2

4-1. Confirmation of Inhibitory Effect of Compound 9-2 on Oxygen Consumption Rate To examine the inhibitory activity of Compound 9-2 described in Example 1-3 on mitochondrial respiration, a change in oxygen consumption rate was measured. More specifically, a mitochondrial oxygen consumption rate (OCR) was measured using a XF24 extracellular flux analyzer (Seahorse Bioscience). HCT-116 cells ($1\times10^5$ cells) were cultured in a culture plate (XF24 cell culture plate) for 24 hours, the culture medium was exchanged with a XF assay medium, and then the cells were incubated in a carbon dioxide-free cell incubator for 1 hour. After the mitochondrial oxygen consumption rate was measured three times in drug-free cells, oxygen consumption rates were measured three times after the administration of oligomycin (1 μM), which is an ATP synthesis inhibitor, three times after the administration of carbonyl cyanide p-trifluoromethoxyphenylhydrazone (0.5 μM), which is a chemical uncoupler, and three times after the administration of rotenone (1 μM) and antimycin A (1 μM), which are electron transport chain inhibitors.

Figure 5:
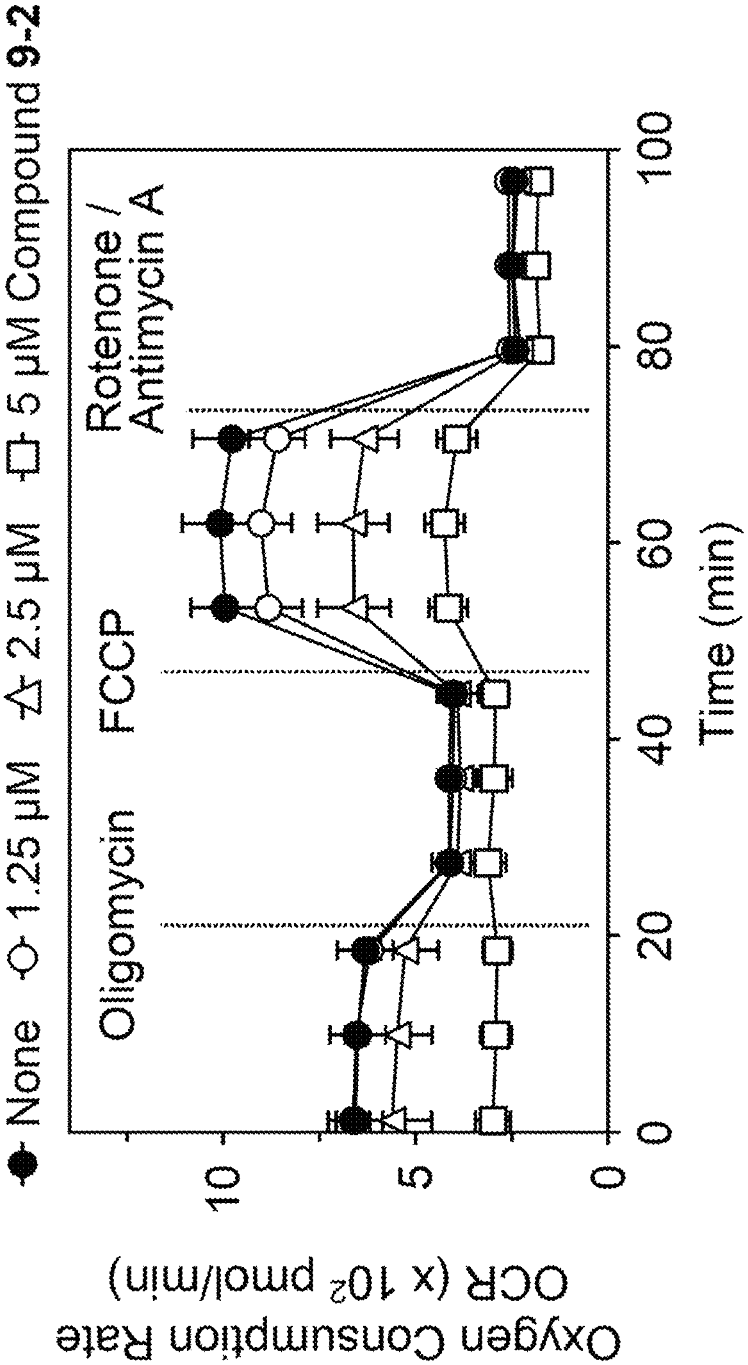
FIG. 5 shows the result of measuring the oxygen consumption rate (OCR) of mitochondria in cancer cells according to a compound of the present invention.

As a result, as shown in FIG. 5, it was confirmed that Compound 9-2 inhibited a mitochondrial oxygen consumption rate in cancer cells, and a basal respiration rate and a maximum respiration rate decrease in a concentration-dependent manner.

4-2. Confirmation of Intracellular Oxygen Increase by Compound 9-2

To confirm an increase in intracellular oxygen concentration by inhibition of a mitochondrial oxygen consumption rate by Compound 9-2 described in Example 1-3, an experiment using an oxygen-sensitive fluorescent probe was performed. More specifically, HCT-116 cells ($1\times10^5$ cells) were treated with Compound 9-2 and hypoxia-sensitive fluorescent probe MAR (Goryo Inc., 0.5 μM), and cultured in a cell incubator under a hypoxia condition for 6 hours. Afterward, an intracellular change in fluorescence intensity by hypoxia was measured and quantified using the IncuCyte® live-cell analysis system (Essen BioScience).

Figure 6:
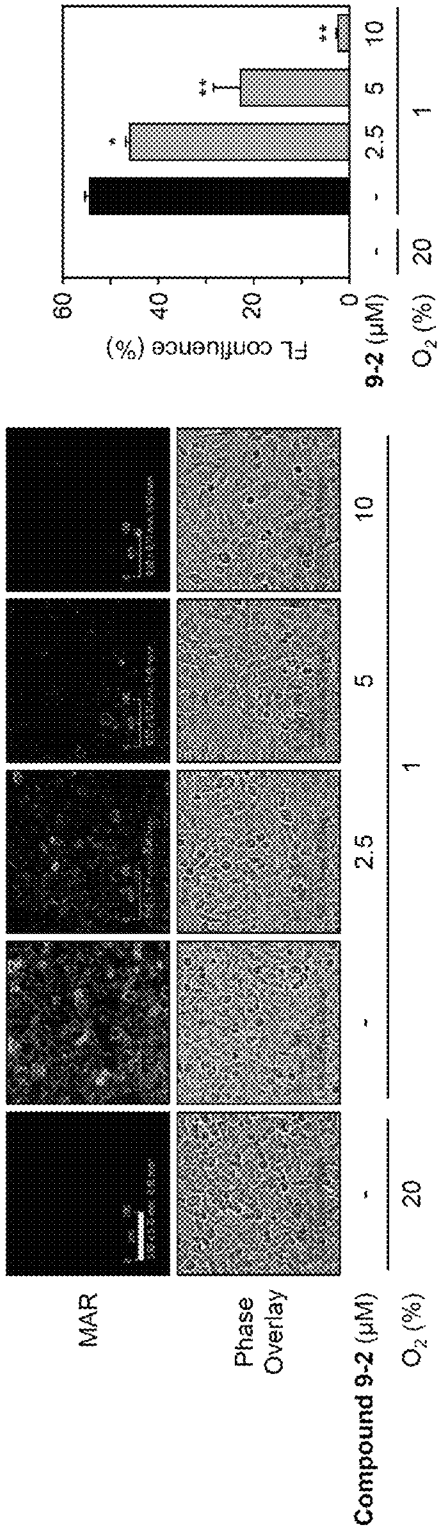
FIG. 6 shows the result of confirming the effect of a compound of the present invention on an increase in oxygen concentration in cells by inhibiting the OCR of mitochondria using an oxygen-sensitive fluorescent probe.

As a result, as shown in FIG. 6, it was confirmed that the intracellular oxygen concentration was increased by Compound 9-2.

Experimental Example 5. Confirmation of Antitumor Effect of Compound 9-2

To confirm an effect of Compound 9-2 on inhibition of cancer cell growth in vivo, an experiment was performed using a cancer cell-transplanted mouse model. More specifically, a plate-cultured HCT-116 colorectal cancer cell line was obtained by trypsin treatment, washed with a serum-free medium, and diluted to a concentration of $2.5\times10^7$ cells/mL. Afterward, the diluted cells ($5\times10^6$ cells/200 μl) were administered to a side of each of seven 6-week-old female nude mice (SLC-Central Lab Animal Inc., Korea), which are specific pathogen-free (SPF) Balb/c mice, through subcutaneous injection. After the tumor size became about 100 $mm^3$, Compound 9-2 was orally administered at a concentration of 20 mg/kg once a day, and on each of day 3, 5, 7, 10, 12, 14, 17, 19, 21, and 24, the body weight and tumor size of the nude mouse were measured using the following Equation 1. After 24 days of Compound 9-2 administration, the mouse was sacrificed to extract the tumor, and then the weight and size of the extracted tumor were confirmed.

$$\text{Tumor size } (mm^3) = \frac{\text{length} \times \text{width} \times \text{height}}{2} \quad \text{[Equation 1]}$$

Figure 7A:
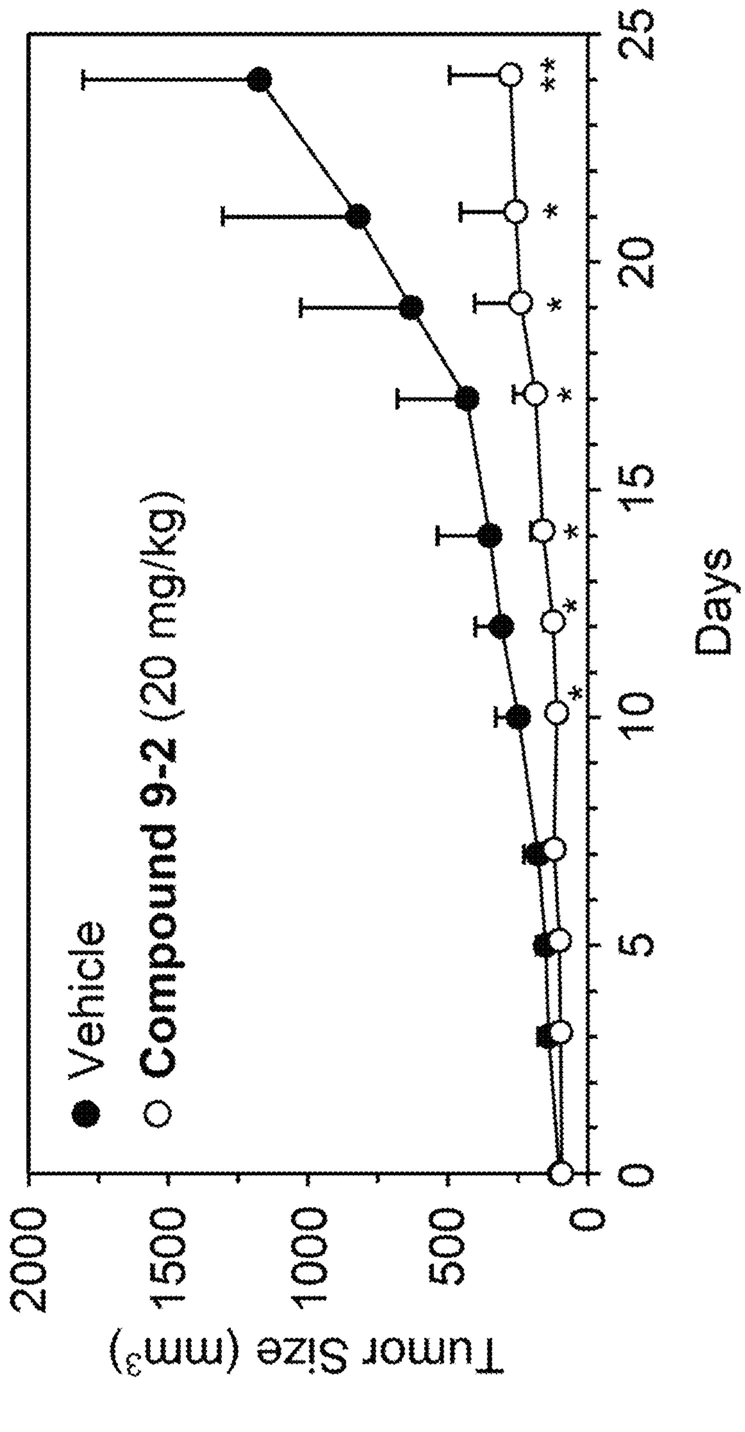
FIGS. 7A and 7B show the results of confirming a decrease in size or volume of a tumor after the administration of a compound of the present invention.
Figure 7B:
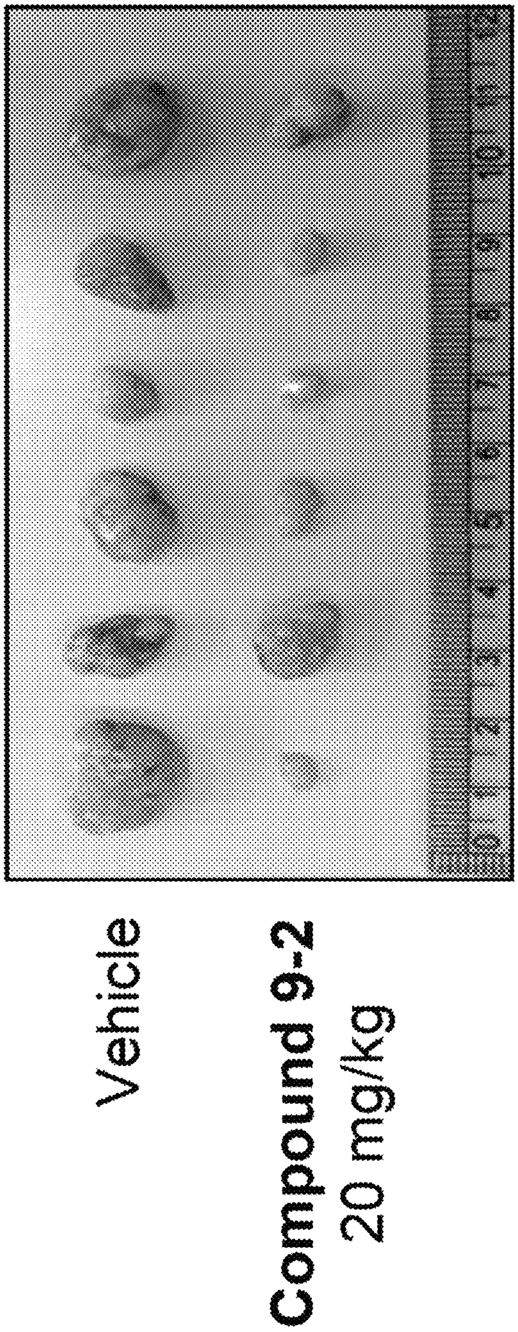
Figure 7C:
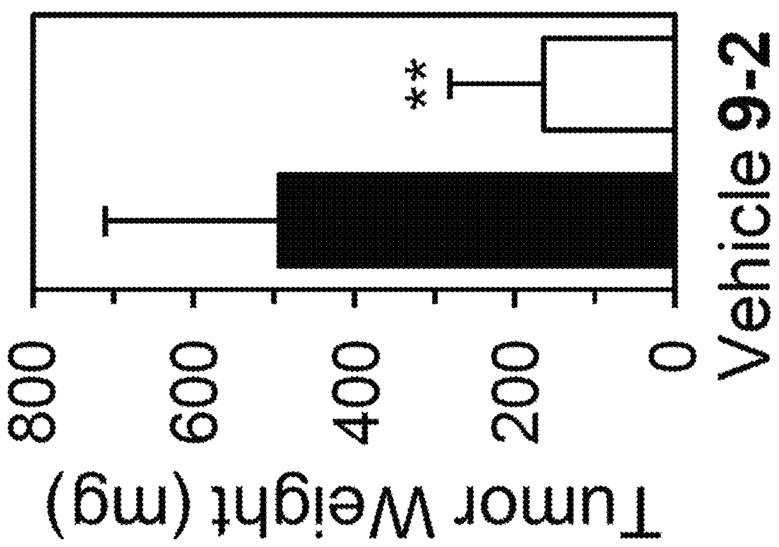
FIG. 7C shows the result of confirming a decrease in weight of a tumor after the administration of a compound of the present invention.

As a result, as shown in Table 2 below, there was no significant change in body weight of the mice after tumor transplantation, and as shown in FIGS. 7A, 7B and Table 3 below, by examining the intracellular antitumor effect of Compound 9-2, it was confirmed that tumor formation (size or volume) was reduced 76.4% in Compound 9-2-treated mice, and as shown in FIG. 7C, after 24 days of Compound 9-2 administration, the tumor weight was 163.0±117.5 mg, which was reduced 67.0%, compared to 493.5±216.5 mg, which is the tumor weight of non-treated mice.

TABLE 2

| | Body weight (g) | |
|---|---|---|
| Time (day) | Vehicle | Compound 9-2 |
| 0 | 21.2 ± 0.9 | 21.2 ± 0.6 |
| 3 | 21.7 ± 0.8 | 21.5 ± 0.8 |
| 5 | 21.9 ± 0.7 | 21.8 ± 0.7 |
| 7 | 21.9 ± 0.9 | 21.6 ± 1.1 |
| 10 | 22.4 ± 0.9 | 22.2 ± 1.0 |
| 12 | 22.9 ± 0.9 | 22.7 ± 0.7 |
| 14 | 22.9 ± 1.0 | 22.7 ± 1.0 |
| 17 | 23.0 ± 1.0 | 22.6 ± 0.8 |
| 19 | 22.6 ± 0.9 | 22.4 ± 0.5 |
| 21 | 23.0 ± 0.9 | 22.5 ± 0.7 |
| 24 | 22.7 ± 0.7 | 22.3 ± 0.8 |

TABLE 3

| | Tumor size ($mm^3$) | |
|---|---|---|
| Time (day) | Vehicle | Compound 9-2 |
| 0 | 102.5 ± 11.0 | 94.1 ± 11.0 |
| 3 | 138.9 ± 38.9 | 97.3 ± 9.8 |
| 5 | 151.7 ± 32.8 | 101.6 ± 15.7 |
| 7 | 177.9 ± 49.2 | 119.9 ± 29.3 |
| 10 | 248.5 ± 82.2 | 111.0 ± 19.0 |
| 12 | 308.7 ± 94.7 | 124.2 ± 35.5 |
| 14 | 351.3 ± 186.4 | 159.9 ± 44.6 |
| 17 | 432.3 ± 248.9 | 187.9 ± 78.5 |
| 19 | 631.8 ± 394.3 | 241.4 ± 162.8 |
| 21 | 822.1 ± 484.1 | 258.3 ± 195.7 |
| 24 | 1175.1 ± 630.5 | 277.5 ± 216.0 |

Experimental Example 6. Confirmation of Cell Proliferation Inhibitory Activity of Compound 9-2

The cell proliferation inhibitory activity of Compound 9-2 prepared according to the example was confirmed. Cell lines used in the experiment are lung cancer cell lines A549 and H1703, colorectal cancer cell lines HCT116 and HT29, liver cancer cell lines Hep3B and HepG2, gastric or stomach cancer cell lines NUGC-3 and AGS, kidney and renal cancer cell lines 786-O and Caki-1, breast cancer cell lines MCF-7 and MDA-MB-231, a prostate cancer cell line PC3, a pancreatic cancer cell line MIA-PaCa-2, a cervical cancer cell line HeLa, and normal cell lines WI-38 and CCD-32Lu. Specifically, each of the cell lines was suspended in DMEM containing 5% FBS, transferred to a 96-well plate ($3\times10^3$ cells/well), and cultured in a 37 □ cell incubator maintaining 5% carbon dioxide for 24 hours. Following treatment of Compound 9-2 at various concentrations, the cells were incubated for 72 hours, fixed with a 10% aqueous formalin solution, and stained with a 0.5% methylene blue solution. Afterward, a change in the concentration of methylene blue extracted with a 0.5% aqueous hydrochloric acid solution was analyzed by measuring absorbance at 600 nm.

As a result, as shown in Table 4, Compound 9-2 inhibited the proliferation of various cancer cells, which are normal cell lines, and particularly, a strong inhibitory effect was exhibited on A549, HCT116 and HepG2 cells. It was confirmed that Compound 9-2 has no effect on the proliferation of normal cell lines within a concentration range in which the proliferation of cancer cells is inhibited.

TABLE 4

| Cells | Viability $GI_{50}$ (μM) |
|---|---|
| A549 | +++ |
| H1703 | ++ |
| HCT116 | +++ |
| HT29 | ++ |
| Hep3B | + |
| HepG2 | +++ |
| NUGC-3 | ++ |
| AGS | + |
| 786-O | + |
| Caki-1 | + |
| MCF-7 | + |
| MDA-MB-231 | + |
| PC3 | + |
| MIA PaCa-2 | ++ |
| HeLa | + |
| WI-38 | − |
| CCD-32Lu | − |

1~5 μM: +++,
5~10 μM: ++,
10~20 μM: +,
>20 μM: −

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A compound represented by Formula 3 below or a pharmaceutically acceptable salt thereof:

[Formula 3]

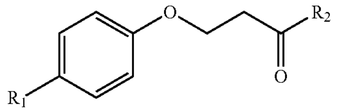

wherein $R_1$ is a nitro group, a trifluoromethyl group, tert-butyl, pentyl, cyclopentyl, cyclohexyl, or 2,4,4-trimethylpentane-2-yl;

$R_2$ is

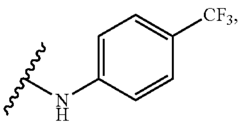

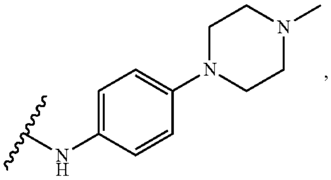
,

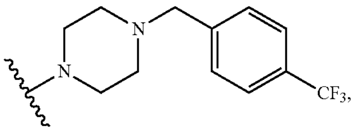

-continued

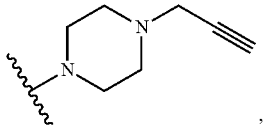
,
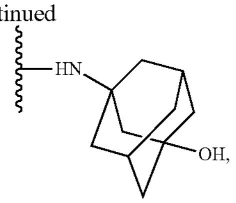
or

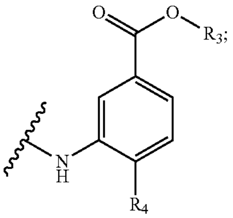

when $R_2$ is

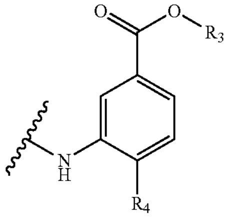

$R_3$ is methyl or 2-propynyl; and $R_4$ is methyl, hydrogen, hydroxyl, methoxy, 2-propynyl,

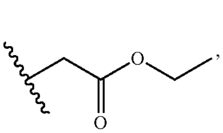
,
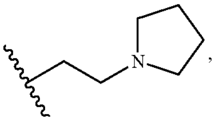
,
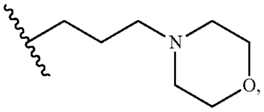

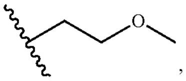
,
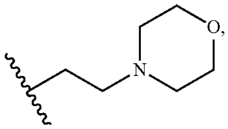
or

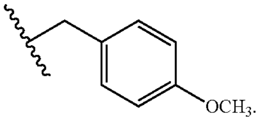

2. A compound selected from the group consisting of the following compounds or a pharmaceutically acceptable salt thereof:

(13) N-(4-(trifluoromethyl) phenyl)-2-(4-(2,4,4-trimethylpentan-2-yl) phenoxy) acetamide;

(14) N-(4-(4-methylpiperazin-1-yl) phenyl)-2-(4-(2,4,4-trimethylpentan-2-yl) phenoxy) acetamide;

(15) 1-(4-(4-(trifluoromethyl) benzyl) piperazin-1-yl)-2-(4-(2,4,4-trimethylpentan-2-yl) phenoxy) ethanone;

(16) 1-(4-(prop-2-ynyl) piperazin-1-yl)-2-(4-(2,4,4-trimethylpentan-2-yl) phenoxy) ethanone;

(17) Prop-2-ynyl 4-hydroxy-3-(2-(4-(2,4,4-trimethylpentan-2-yl) phenoxy) acetamido) benzoate;

(24) methyl 4-methoxy-3-(2-(4-(2,4,4-trimethylpentan-2-yl) phenoxy) acetamido) benzoate:

(53) N-(3-(Morpholine-4-carbonyl) phenyl)-3-(4-(2,4,4-trimethylpentan-2-yl) phenoxy) propanamide;

(54) Ethyl 2-(3-(3-(4-(2,4,4-trimethylpentan-2-yl) phenoxy) propanamido) benzamido) acetate; and

(55) (S)-methyl 3-methyl-2-(3-(3-(4-(2,4,4-trimethylpentan-2-yl) phenoxy) propanamido) benzamido) butanoate.

3. A pharmaceutical composition for treating cancer, comprising the compound of claim 1 or a pharmaceutically acceptable salt thereof as an active ingredient;

wherein the cancer is selected from the group consisting of lung cancer, small-cell lung cancer, non-small cell lung cancer, adenocarcinoma of the lung, squamous carcinoma of the lung, hepatocellular cancer, gastric or stomach cancer, gastrointestinal cancer, pancreatic cancer, cervical cancer, ovarian cancer, liver cancer, hepatoma, breast cancer, colon cancer, rectal cancer, colorectal cancer, endometrial or uterine carcinoma, kidney and renal cancer, prostate cancer, vulval cancer, hepatic carcinoma, biliary tract cancer, and colorectal cancer.

4. The pharmaceutical composition of claim 3, wherein the composition simultaneously inhibits any one or more activities of malate dehydrogenase 1 (MDH1) and dehydrogenase 2malate dehydrogenase 2 (MDH2).

* * * * *